United States Patent [19]
Fergason et al.

[11] Patent Number: 5,857,215
[45] Date of Patent: *Jan. 12, 1999

[54] HELMET WITH HIGH PERFORMANCE HEAD AND FACE PROTECTION UTILIZING MOLDED COMPOSITE MATERIALS AND METHOD

[75] Inventors: Jeffrey K. Fergason, Menlo Park; John D. Fergason, Mountainview, both of Calif.

[73] Assignee: ILIXCO, Inc., Menlo Park, Calif.

[ * ] Notice: The term of this patent shall not extend beyond the expiration date of Pat. No. 5,749,096.

[21] Appl. No.: 599,733

[22] Filed: Feb. 12, 1996

Related U.S. Application Data

[63] Continuation-in-part of Ser. No. 270,633, Jan. 7, 1994, Pat. No. 5,749,096.

[51] Int. Cl.⁶ ........................................ A42B 3/00
[52] U.S. Cl. ........................................ 2/8; 2/412
[58] Field of Search .................. 2/7, 8, 9, 412, 2/5, 2.5, 425, 410, 411; 264/222

[56] References Cited

U.S. PATENT DOCUMENTS

| | | | |
|---|---|---|---|
| D. 349,588 | 8/1994 | Howard et al. . | |
| D. 353,692 | 12/1994 | Fergason et al. . | |
| 3,868,872 | 3/1975 | La Marre et al. | 2/8 |
| 3,983,306 | 9/1976 | Nielinger et al. | 428/474 |
| 4,075,717 | 2/1978 | Lemelson | 2/412 |
| 4,300,242 | 11/1981 | Nava et al. | 2/412 |
| 4,391,924 | 7/1983 | Uram, Jr. | 521/178 |
| 4,466,138 | 8/1984 | Gessalin | 2/410 |
| 4,473,208 | 9/1984 | Nava | 249/65 |
| 4,656,674 | 4/1987 | Medwell | 2/412 |
| 4,693,678 | 9/1987 | Von Volkli | 425/405 |
| 4,728,173 | 3/1988 | Toth | 350/332 |
| 4,734,940 | 4/1988 | Galet et al. | 2/422 |
| 4,845,786 | 7/1989 | Chiarella | 2/412 |
| 4,853,973 | 8/1989 | Boochard | 2/8 |
| 4,908,877 | 3/1990 | White | 2/412 |
| 4,950,445 | 8/1990 | Salce et al. | 264/549 |
| 4,953,234 | 9/1990 | Li et al. . | |
| 5,018,220 | 5/1991 | Lane et al. | 2/5 |
| 5,062,156 | 11/1991 | Siegal | 2/8 |
| 5,074,647 | 12/1991 | Fergason et al. | 359/63 |
| 5,119,516 | 6/1992 | Broersma | 2/411 |
| 5,208,688 | 5/1993 | Fergason et al. | 359/53 |
| 5,224,219 | 7/1993 | Edwards et al. | 2/8 |
| 5,248,880 | 9/1993 | Fergason | 250/205 |
| 5,252,817 | 10/1995 | Fergason et al. | 250/205 |
| 5,347,893 | 9/1994 | Dunn | 2/2.5 |
| 5,377,032 | 12/1994 | Fergason et al. | 359/62 |
| 5,421,035 | 6/1995 | Klose et al. | 2/411 |
| 5,477,563 | 12/1995 | Gentes et al. | 2/411 |
| 5,522,198 | 6/1996 | Byer et al. | 2/8 |
| 5,548,848 | 8/1996 | Huybrechts | 2/425 |

FOREIGN PATENT DOCUMENTS

WO9014809 12/1990 WIPO .

*Primary Examiner*—Michael A. Neas
*Attorney, Agent, or Firm*—Renner, Otto, Boisselle & Sklar

[57] ABSTRACT

A welding helmet having high structual integrity is formed of a single sheet of composite material, such as Kevlar fabric impregnated with a phenolic thermoset resin; a viewing port in the front of the helmet includes a welding lens is either of fixed or automatically darkening type; and curves, bends, folds and steps in the composite material and trim pieces in the viewing port area and about the peripheral rim of the helmet shell provide additional stiffening for the helmet. A method of making a welding helmet of a single sheet of composite material includes pre-forming the composite material to a shape similar to that of the finished molding helmet shape, and placing the pre-shaped composite material in a compression mold and closing the mold to mold the composite material to shape while curing the composite material by applying heat other otherwise assisting in the curing of the composite material; and mounting a welding lens in a viewing port of the welding helmet.

65 Claims, 10 Drawing Sheets

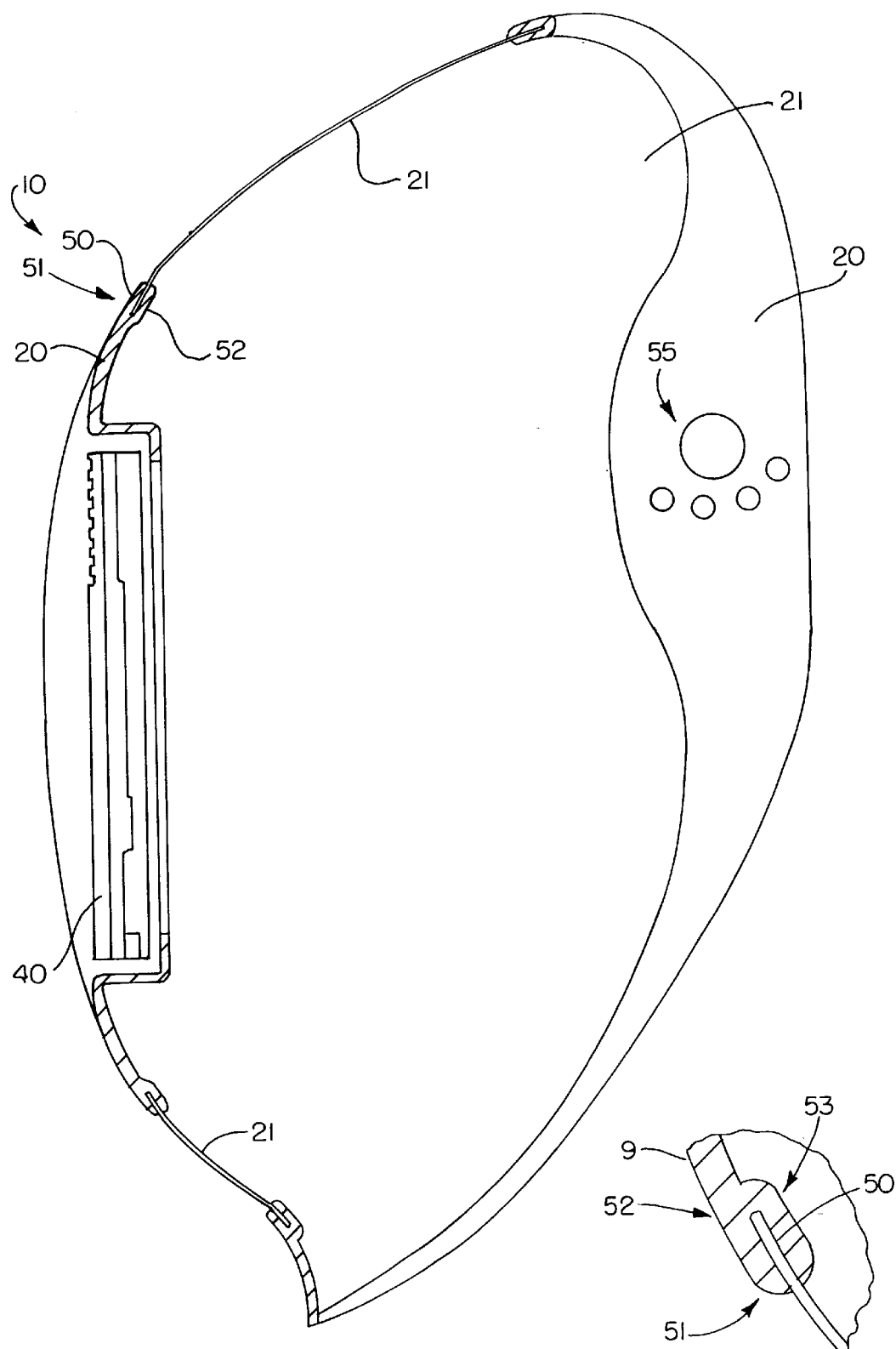

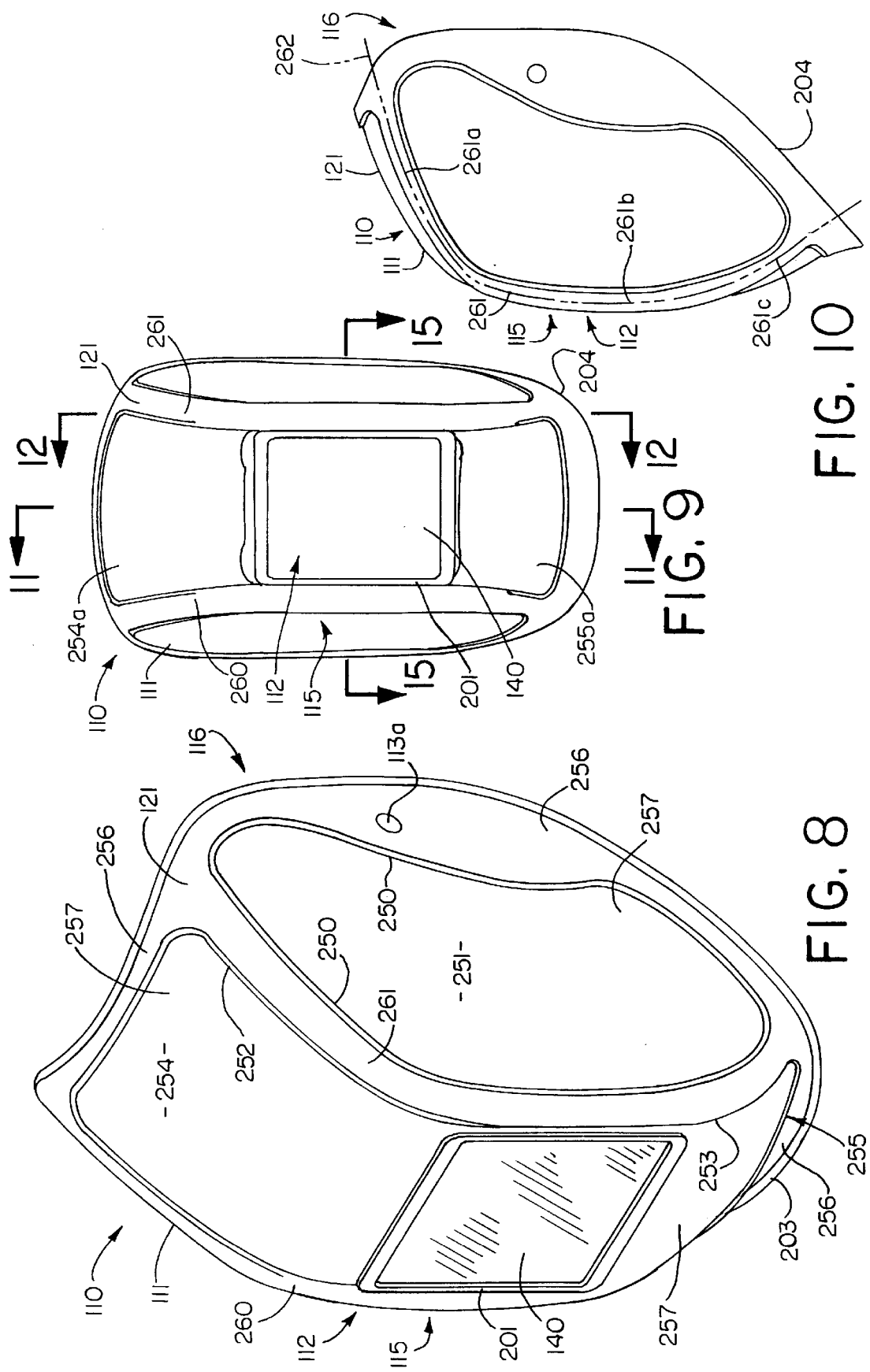

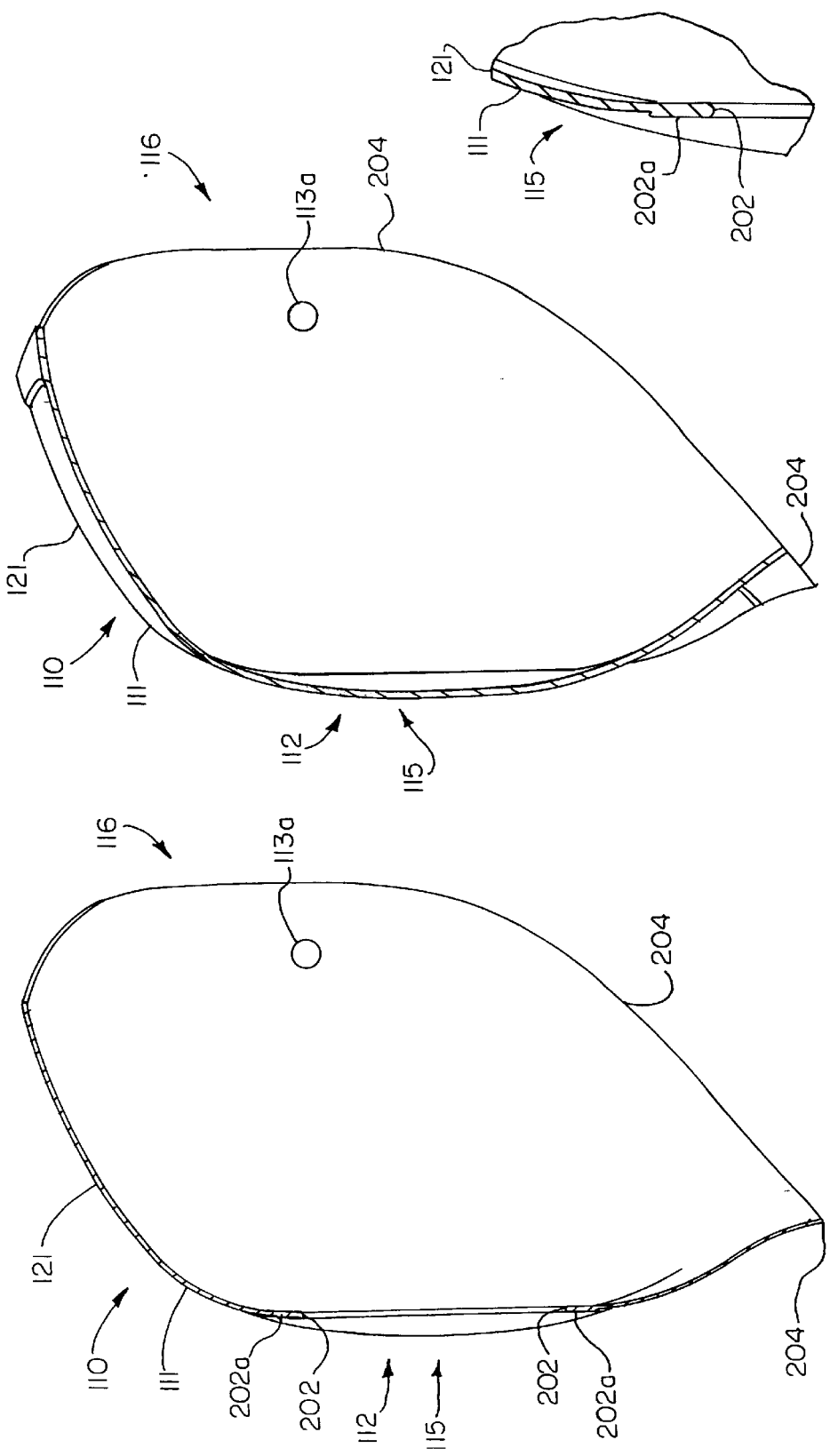

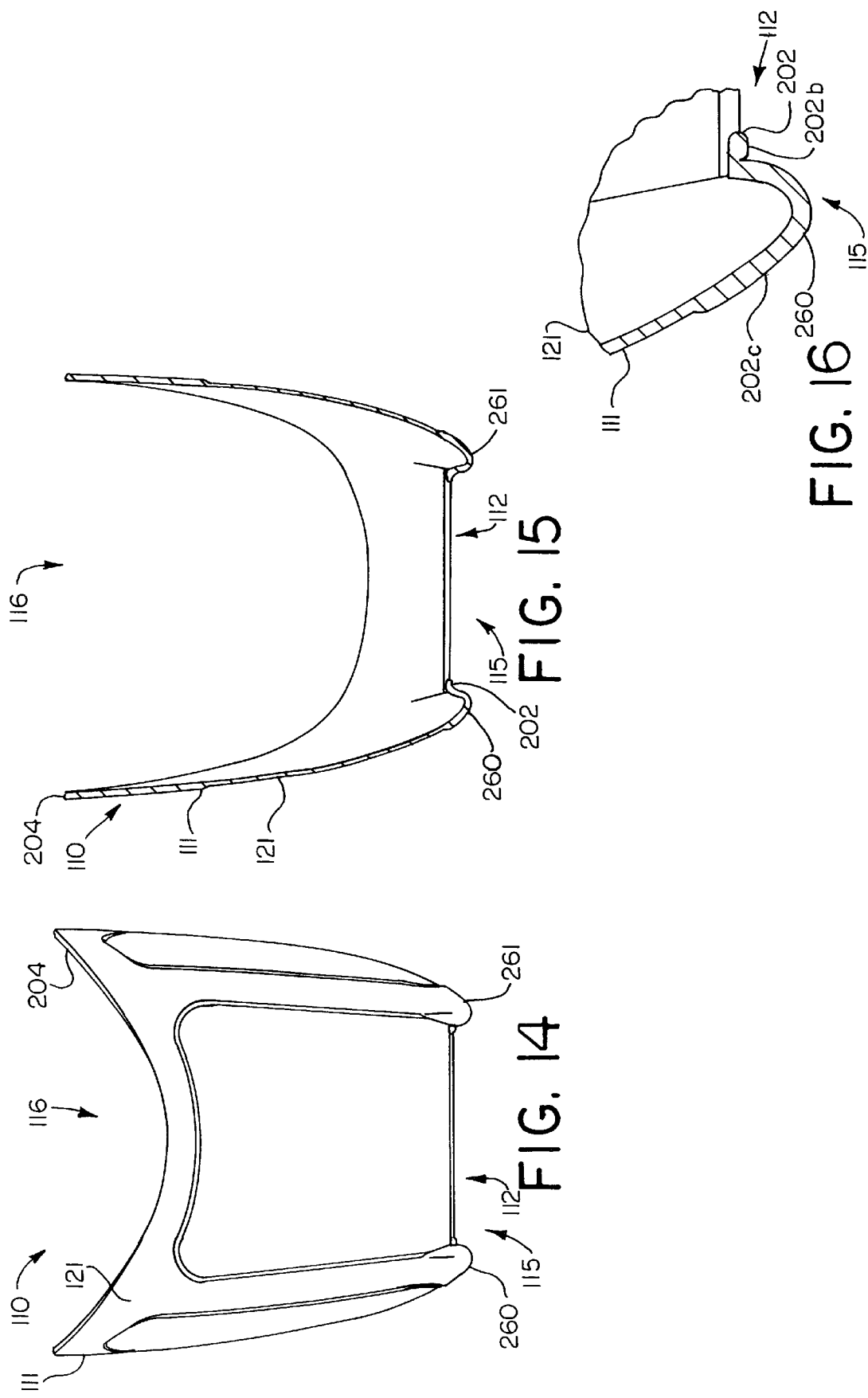

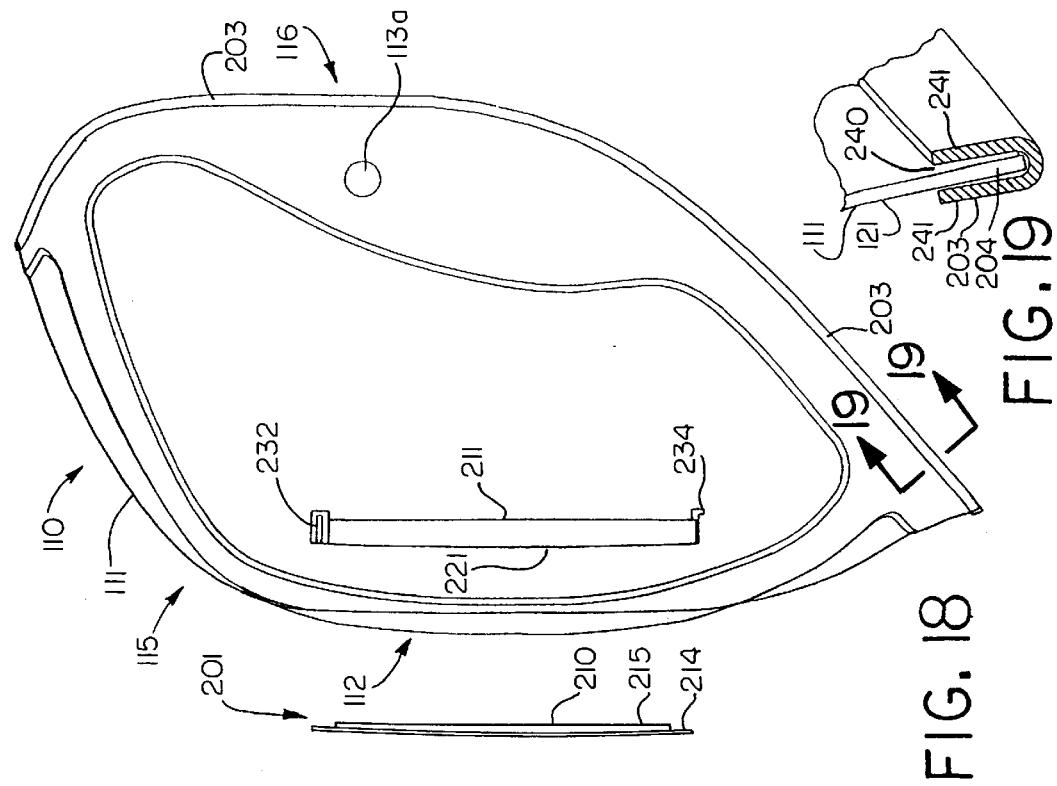
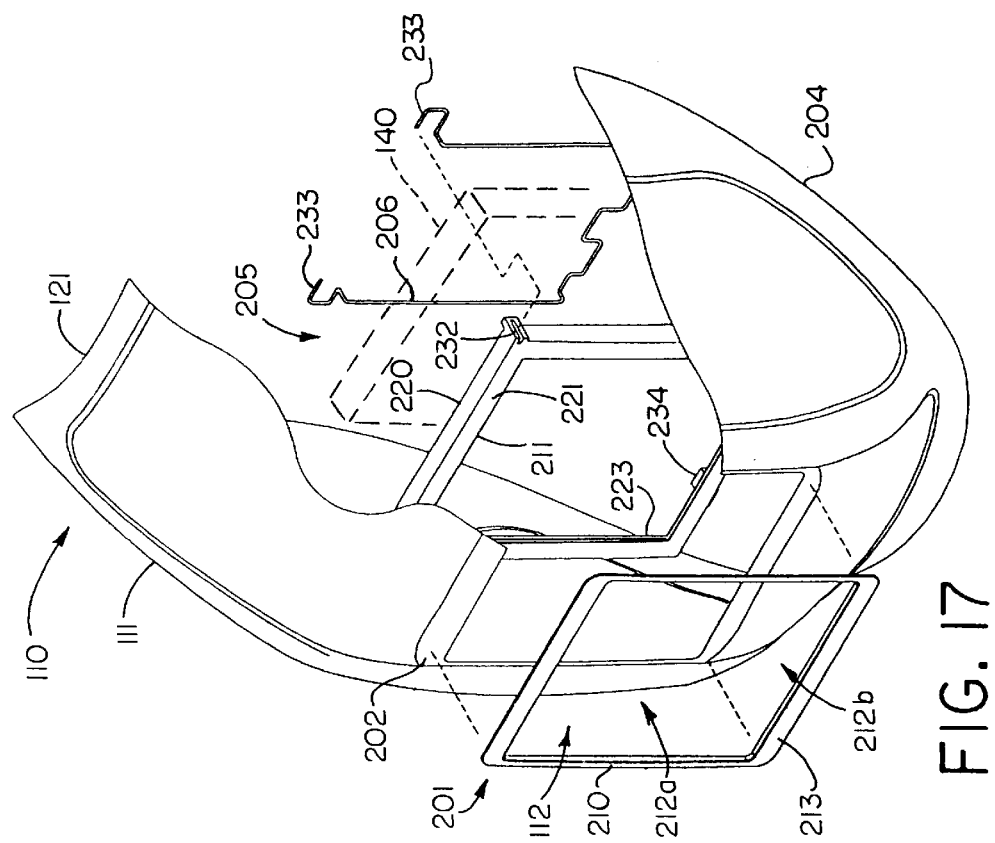

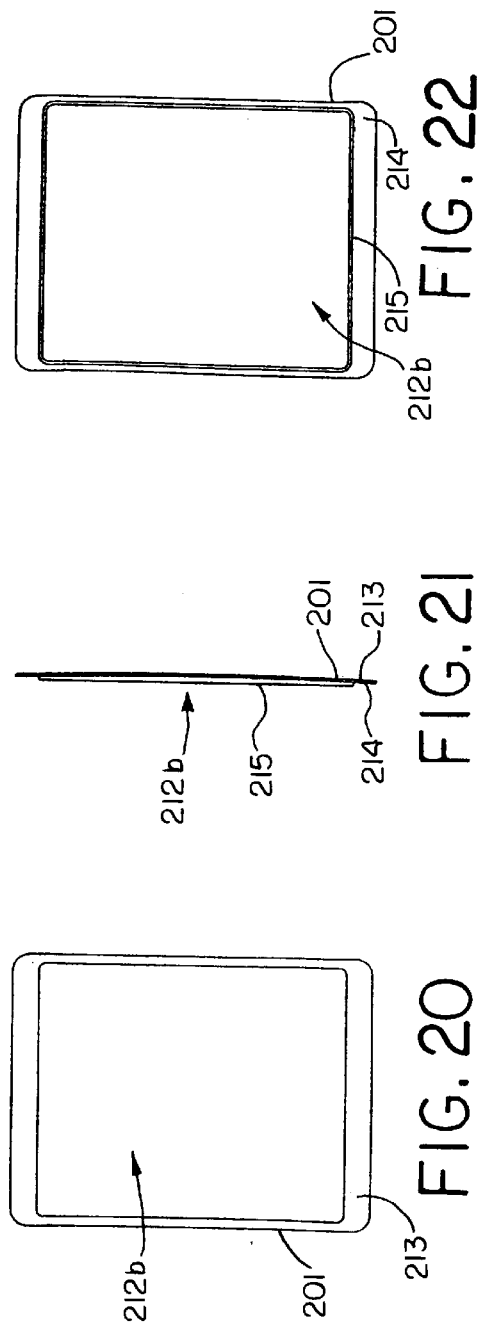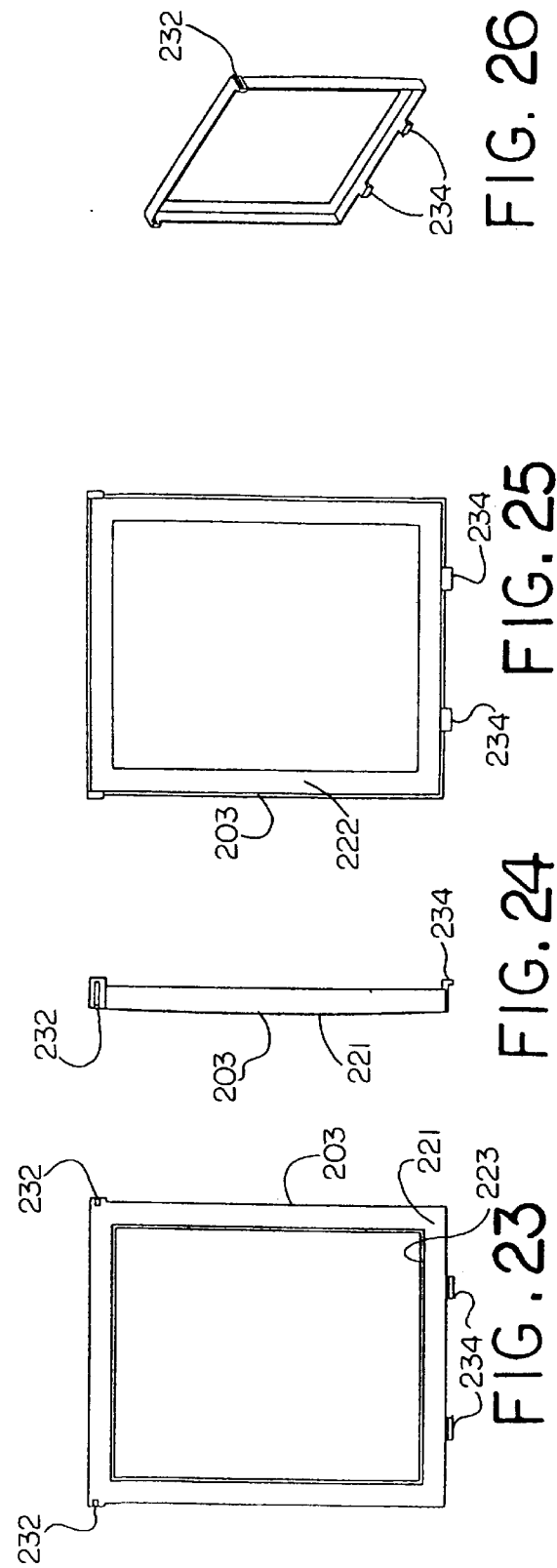

HELMET WITH HIGH PERFORMANCE HEAD AND FACE PROTECTION UTILIZING MOLDED COMPOSITE MATERIALS AND METHOD

This is a continuation-in-part of copending U.S. patent application Ser. No. 08/270,633, filed Jan. 7, 1994, now U.S. Pat. No. 5,749,096, the entire disclosure of which hereby is incorporated by reference.

TECHNICAL FIELD

The present invention relates generally, as is indicated, to structures formed of a composite material, to a method of molding such structures of composite material, and, more particularly, to head and face protection devices utilizing molded composite materials. Exemplary head and face protection devices include welder's shields and helmets.

BACKGROUND

Welders and others wear welding helmets, face shielding devices, etc., to protect themselves from strong ultraviolet, visible and/or infrared light rays that are emitted from a welding arc. As used herein light may mean electromagnetic energy in the ultraviolet, visible and/or infrared ranges. Welding helmets also provide a protective barrier between the welder and the welding arc fumes, heat, hot metal spatter, sparks, and possibly other flying debris.

An example of a welding helmet includes an outside shell with a viewing port, a mounting head band, and means for mounting a welding lens in the viewing port such as a viewing port filter plate retainer mechanism. The viewing port may include a darkened piece of glass, plastic or other material often referred to as a lens or as a welding lens, the object of which is to permit viewing of a welding operation while protecting the eyes of the welder from the ultraviolet, visible, and/or infrared light occurring during a welding operation. The lens may be of the automatic type which darkens to block such light during welding and which lightens to transmit more light when welding is not occurring. Examples of such automatic welding lenses are disclosed in U.S. Pat. Nos. 5,074,647, 5,208,688; 5,248,880; and 5,252,817; the entire disclosures of which are hereby incorporated by reference. Other types of automatic welding lenses and fixed welding lenses may be used in welding helmets, as is known.

Various mounting headbands have been used to mount a welding helmet, etc. on the head of a person. Modern headbands are adjustable to head size and some are attached to and mounted on a welding helmet to permit relative pivoting movement to allow the helmet to be opened and/or to allow the helmet to be placed comfortably and securely on the head. A pivoting connection between the mounting headband and a welding face shield device, for example, also is used to enable tilting of the face shield between a down position in front of the face and an up position above the top of the head.

Welding helmet shells that are currently made are constructed primarily either of thermoplastic injection molded resins or blends; formed fiberglass or sheet resin materials; or pattern cut and fastened vulcanized fiberboard. These materials have been suitable for welding helmet construction because they offer adequate temperature and impact resistance, but they all are relatively heavy, usually weighing more than 0.5 pounds for the shell only. It would be desirable to reduce the weight of a welding helmet or like device. It also would be desirable to improve the resistance of a welding helmet to hot metal spatter and to sparks and to improve the durability and ability to withstand severe impacts.

Composite material as referred to herein means, for example, a material created from a fiber (or reinforcement) and an appropriate matrix material in order to provide, preferably to maximize, specific performance properties. The constituents do not dissolve or merge completely but retain their identities as they act in concert. Examples of composite material in the context of the present invention include woven fiber, such as that sold under the trademark Kevlar, embedded in a resin matrix, such as epoxy, polyimide, or polyester or other matrix materials. Kevlar material is an aramid fiber sold by DuPont. Such woven fiber and resin may form a single ply or a multiple ply (laminate) structure. The composite material used has characteristics enabling it to be molded, for example, in the manner described herein. Kevlar composite material that includes a woven fiber of Kevlar and a resin or other matrix, adhesive or support type material usually was not able to be conveniently molded in the past to form structures, such as welding helmets. For example, stiffness of the composite material and the relatively poor bonding with the resin, etc., made molding of such structures relatively difficult or impossible. It would be desirable to mold such structures from composite material, such as Kevlar material, to facilitate, expedite and reduce the cost of making such structure from such composite material and/or to enable the manufacturing of such structures from such composite material. Other exemplary composite materials are described below.

Although composite materials have a number of advantageous characteristics, such as light impermeability, especially when including a dye or other light blocking material, light weight, temperature resistance, and durability, other characteristics, several of which are mentioned below, make them undesirable for use in welding helmets, hard hats, other face shielding devices, and other devices where structural integrity or continuity of shape are required. The cost to obtain the composite material thickness that is required for strength of the particular object is often prohibitive for their use. Such cost may be due to the amount of material required for structural integrity, stiffness, and impermeability. For example, bullet proof vests, rocket nozzles and rocket fins/control surfaces made of Kevlar material usually are formed of several layers that are laid up (placed in layers) in a mold, and this labor intensive process is time consuming and expensive. Also, such laid up material often must cure in the mold for a relatively long time, sometimes an hour or more, which is time consuming and expensive.

It would be desirable to increase the utility of such composite materials, especially by making them easily used in devices which require such structural integrity. Examples of such devices may well be welding helmets, hard hats, face shielding devices, and/or other devices used for protective purposes, such as those mentioned above, and/or for other purposes.

Furthermore, it is difficult and sometimes not possible to form mechanical details or features in composite materials. An exemplary mechanical feature may be a support device, a support opening, and/or a threaded opening structure for connecting a mounting headband to a welding helmet shell. For example, due to the lack of rigidity and/or the relative impenetrability of composite material of Kevlar and resin it is difficult to form such details or features, and such details and features may not hold up during use of the structure. It would be desirable to provide in a device that uses such composite material, mechanical details for fastening, reinforcement, and/or other purposes.

Composite materials also tend to have relatively ragged or unsmooth edges, and various techniques have been used in the past to finish those edges to provide a smooth edge. Rough edges are undesirable because they can help cause the breakage of the composite panel upon side impact. It would be desirable to facilitate finishing such edges to provide smooth surfaces that are less likely to encounter breakage as well as to cause a potential hazard to the user.

A disadvantage of using a dyed material, such as fiberglass and a dyed resin as a welding helmet is the light permeability of the dyed material. The dye absorbs light but, may not block all transmission. It would be desirable to increase light blocking effectiveness of a welding helmet. Various of the above difficulties and/or disadvantages to use Kevlar composite material or the like are addressed in copending U.S. patent application Ser. No. 08/270,633. In that application is disclosed a structure of composite material and a plastic injection molded frame insert molded to the composite material. A complicating factor in such insert molding method can be shrinkage of the molded plastic material, which may distort the shape of the molded structure, e.g., welding helmet, and/or reduce strength characteristics. Another such factor may be knit lines where plastic flouring from different directions comes together and "knits"; sometimes structural weakness may occur and lessen lines. Although close or accurate control of the molded material, design and/or molding conditions, e.g., temperature, flow rates, pressure, etc., may alleviate these difficulties, it would be desirable to avoid them without the need for such close control of insert molding material and process.

Another possible disadvantage of such insert molding technique of the mentioned patent application is the added weight of the molded frame or rib members relative to the lighter weight composite material. It would be desirable to minimize weight of a welding helmet.

SUMMARY

One aspect of the invention relates to a structure comprising a composite material molded as an integral structure.

According to another aspect, a device, such as a welding helmet or the like, for providing protection for a person, includes a single sheet of light with composite material which is molded to the shape of the welding helmet, a welding lens in the viewing port of the helmet and a mounting structure for positioning the device on a person.

An additional aspect relates to a light weight device for protecting a part of the body of a person including a relatively light weight composite material molded to shape and bends in the structure for providing stiffness generally to maintain shape of the device.

Another aspect relates to reducing the weight of a welding helmet or the like by molding the helmet from a single sheet or an integral sheet of composite material without the need for substantial frame members to secure together respective portions of the composite material.

A further aspect is to avoid knit lines in plastic that has flowed as part of an injection molding process to form frame members of a welding helmet, and, thereby, avoid the possible weakness introduced by such knit lines.

Yet a further aspect is to expedite manufacturing of a welding helmet or the like by molding the shell of the helmet as a single piece of composite material and subsequently providing at respective edges trim pieces for protection and/or stiffening.

An additional aspect relates to a light weight device for protecting a part of the body of a person including a relatively light weight composite material molded to shape and bends in the structure for providing stiffness generally to maintain accurate location, strength and/or durability of mechanical features of the device.

Yet a further aspect relates to a welding helmet including a shell of molded composite material and a viewing port mounted in the shell.

A further aspect relates to a protective device for a person comprising composite material molded with gradual substantially unidirectional bends providing shape and stiffness and facilitating molding of the composite material.

Yet an additional aspect relates to a method for making a structure using a sheet-like composite material including placing the composite material in a mold, applying pressure to the composite material to urge it to a shape configured by the mold, and removing the molded composite material from the mold.

Yet an additional aspect relates to a method for making a protective structure, such as a welding helmet, using a sheet-like composite material including placing the composite material in a mold, applying pressure to a substantial portion of the composite material to urge it to a shape configured by the mold, and placing a trim about at least a substantial portion of the perimeter of the molded structure.

Still another aspect relates to a multiple step method of molding composite material including pre-forming the composite material from a first shape generally to a predetermined shape to facilitate molding the composite material to a final shape, and placing the pre-formed composite material in a mold, applying pressure to the composite material to shape it to a shape approximating that of the mold, and removing the composite material from the mold.

Still another aspect relates to a method of molding composite material of woven Kevlar material and resin material to form a welding helmet or other protective structure for a person, including bending the composite material in a mold about surfaces that are relatively gradually curved in a sufficiently gradual manner to allow for draping of the material substantially without wrinkles or binding. An exemplary model of such a gradually curved structure is gradually curved primarily in one direction and is substantially less curved (or has a substantially larger radius of curvature) in a different direction. Drapability of the fabric depends on the weave of the material. The more drapable the weave, the sharper the curve possible.

Still another aspect relates to a method of maintaining shape of a welding helmet or other structure formed of molded composite material, comprising using bent surface area portions between adjacent relatively more planar surfaces to provide stiffening to retain shape.

One aspect of the invention relates to a structure comprising a composite material and a support material, the support material being integrally coupled to the composite material to form an integral structure.

According to another aspect, a device for providing protection for a person includes a sheet-like composite material and a frame structure, the frame structure integrally bonded to the sheet-like composite material, and a mounting structure for positioning the device on a person. A further aspect relates to a device for providing protection for a person including a sheet-like composite material and a frame structure, the frame structure integrally molded to the sheet-like composite material, and a mounting mechanism for positioning the device on a person.

An additional aspect relates to a light weight device for protecting a part of the body of a person including a plurality of relatively light weight panels of composite material and a frame structure for holding the panels in relatively fixed relation.

Still another aspect of the invention concerns protective gear for a person including a plurality of sheet-like panels of composite material and a frame insert molded directly to respective panels for holding the panels in relatively fixed position.

Yet a further aspect relates to a welding helmet including a plurality of panels of composite material, a frame structure of thermoplastic material securely adhered to the composite material by insert molding thereto, and a viewing port.

Yet an additional aspect relates to a method for making a structure using a sheet-like composite material including adhering to the composite material a relatively rigid support member.

Even another aspect of the invention relates to a method of making a device formed of a composite material and a frame including the steps of placing a sheet-like quantity of the composite material in a mold of a molding machine, placing material for forming the frame in the mold, and molding the frame directly to the composite material.

The foregoing and other objects, features, aspects and advantages of the invention will become more apparent as the following description proceeds. It will be appreciated that while embodiments of the invention are described herein, the scope of the invention is to be determined by the claims and equivalents thereof. Also, although the invention is described with respect to a welding helmet, it will be appreciated that the concepts of the invention may be utilized in conjunction with other devices.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be suitably employed.

BRIEF DESCRIPTION OF THE DRAWINGS

In the annexed drawings:

FIG. 3 is a partial side elevation section view of the welding helmet of FIG. 1;

FIG. 4 is an enlarged fragmentary section view of a junction between composite material and support material of the invention;

FIG. 8 is a perspective view of another embodiment of the welding helmet formed of a single piece of molded composite material;

FIG. 9 is a front elevation view of the welding helmet of FIG. 8;

FIG. 10 is a side elevation view of the welding helmet of FIG. 8;

FIG. 11 is a side section view of the welding helmet looking in the direction of the arrows 11—11 of FIG. 9;

FIG. 12 is a section view of the welding helmet looking in the direction of the arrows 12—12 of FIG. 9;

FIG. 13 is an enlarged section view of a portion of the welding helmet as shown in FIG. 11 adjacent the upper part of the viewing port;

FIG. 14 is a top view of the welding helmet of FIG. 8;

FIG. 15 is a top section view of the welding helmet looking in the direction of the arrows 15—15 of FIG. 9;

FIG. 16 is an enlarged fragmentary section view of a portion of the welding helmet as shown in FIG. 15 adjacent an edge of the viewing port;

FIG. 17 is an exploded isometric view, partially broken away, of the welding helmet of FIG. 8 showing the viewing port and mounting structure for a welding lens cartridge assembly;

FIG. 18 is a side elevation view of the welding helmet of FIG. 8 partly broken away in the area of the viewing port to show the unassembled rim mounting structure for the viewing port and for mounting the welding lens cartridge assembly;

FIG. 19 is an enlarged fragmentary section view of the edge trim for the welding helmet;

FIGS. 20, 21 and 22 are, respectively, front, side and back elevation views of the annular face part of the mounting structure;

FIGS. 23–25 are, respectively, front, side and back elevation views of the annular mounting part of the mounting structure;

FIG. 26 is an isometric view of the annular mounting part of the mounting structure;

DESCRIPTION

Figure 1:
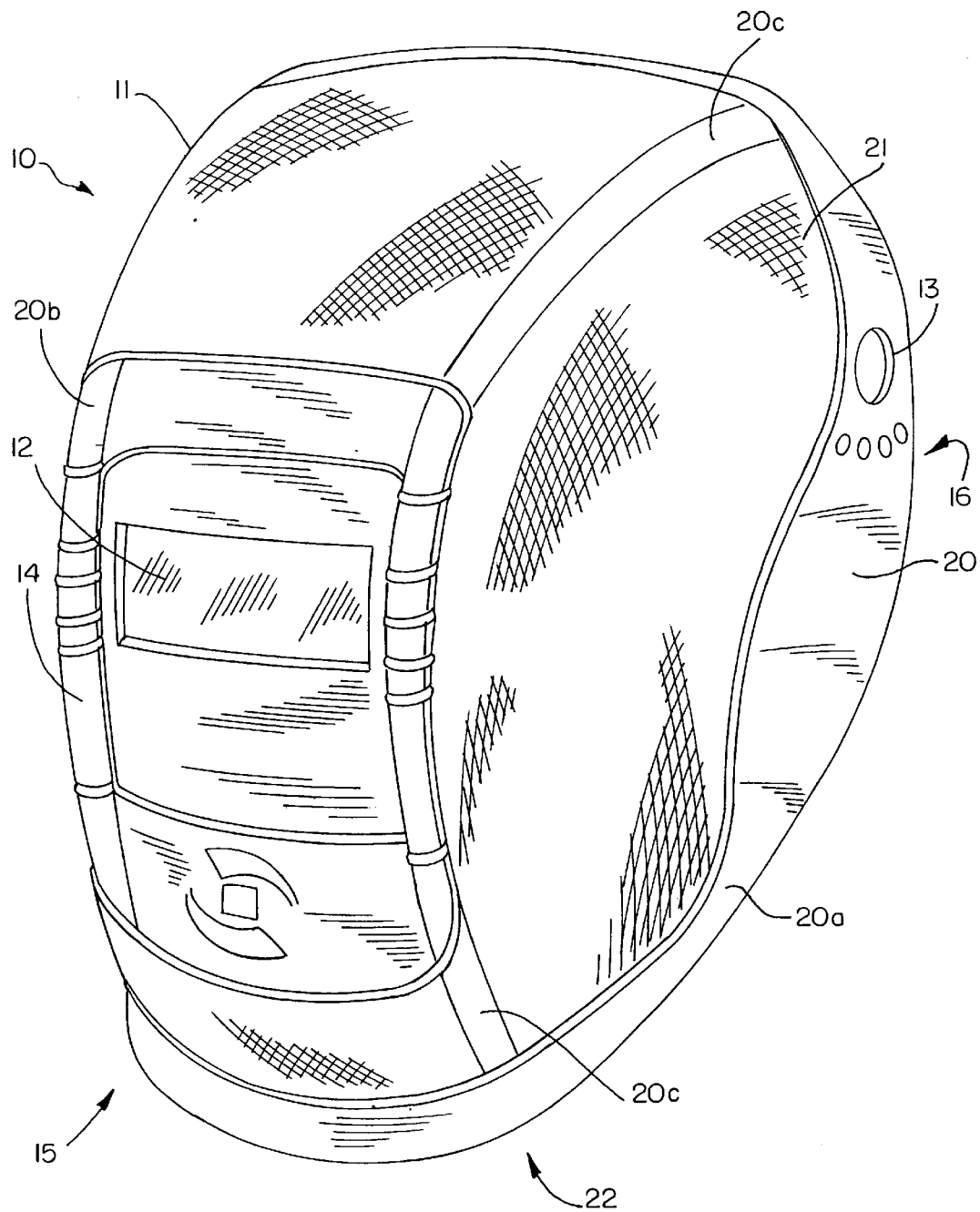
FIG. 1 is an isometric view of a welding helmet in accordance with an embodiment of welding helmet as regards to the present invention in which a frame is insert molded to composite material.

Referring, now, to the drawings, wherein like reference numerals designate like parts in the several figures, and initially to FIG. 1, a welding helmet in accordance with an embodiment of the present invention, as also is disclosed in U.S. patent application Ser. No. 08/270,633, is generally indicated at 10. The welding helmet 10 includes an outside shell 11, a viewing port 12 and viewing port filter/coverplate retainer mechanism 12, a mounting headband (not shown), and the headband pivot connection 13. The welding helmet 10 is intended to be mounted on the head of a person by placing the headband (not shown) onto the head and orienting the welding helmet to place the viewing port 12 at the front 15 of the helmet in front of the person's eyes. The back 16 of the welding helmet may be open in which the case the outside shell 11 may be pivoted about pivot holes 13a of the headband pivot connection 13 in a generally clockwise direction relative to the illustration of FIG. 1 to expose the face of the person wearing the welding helmet. Alternatively, the back 16 may be closed to provide additional isolation and/or protection for the head and face of the person wearing the welding helmet, e.g., while ventilating equipment provides fresh air for breathing.

The outside shell 11 includes a thermoplastic frame 20 and a composite material panel 21. As is seen in FIG. 1, the thermoplastic frame 20 has two primary portions 20a, 20b. The thermoplastic frame 20 may have additional portions, too. The frame portion 20a is at the back 16 of the shell 11 and also at the bottom 22. The frame portion 20b is at the front 15 of the shell 11. The frame portion 20a includes a mechanical detail in the form of an opening for mounting the headgear or mounting headband via the pivot mechanism 13 to the shell. The frame portion 20b provides a mechanical detail for the attachment of the viewing port filter/coverplate retaining mechanism 14 to the shell 11. Additional frame members 20c in the form of web or strut-like members interconnect the frame portions 20a, 20b. Although only several of the strut members 20c are seen in FIG. 1, it will be appreciated that more or fewer than those shown may be used in the welding helmet 10 to interconnect various portions of the frame 20 and also to provide adequate structural support for the composite material 21.

Figure 2:
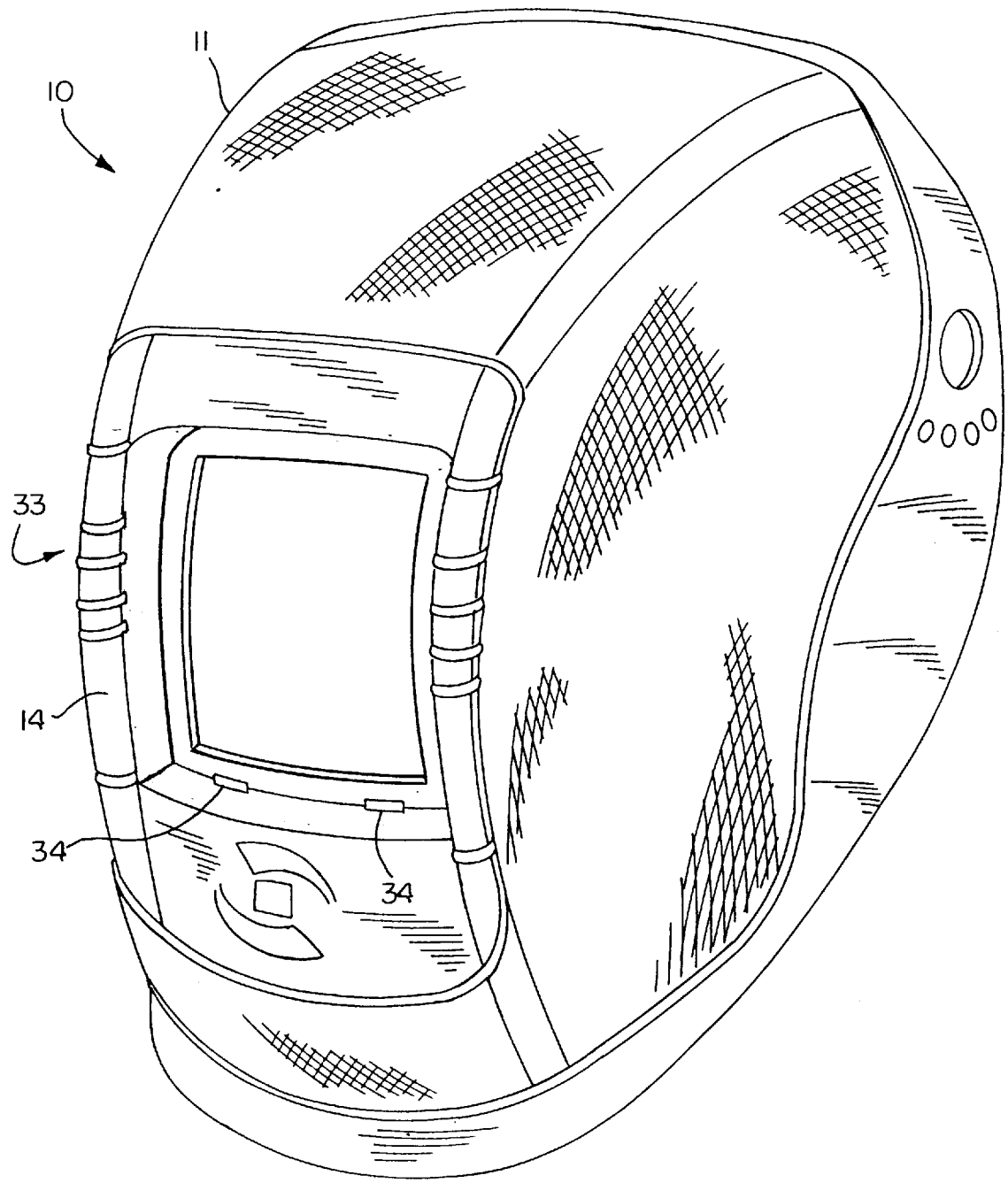
FIG. 2 is an isometric view similar to the drawing of FIG. 1 but with the welding filter coverplate assembly removed to show a mounting structure therefore.

As is seen in FIG. 2, the viewing port retaining mechanism 14 has been removed to expose the open area 33 where the viewing port 12 and particularly the filter/coverplate assembly 14 thereof would be installed. Hinge pivot points 34 are schematically shown for mounting the viewing port filter/coverplate assembly 14 in the area 33. Although only one pair of hinging points 34 is shown at the bottom of area 33 of the viewing port filter plate retainer mechanism 14, additional hinges (not shown) may be included at the top, and/or other mounting mechanism may be used to secure a welding lens cartridge 40 (FIG. 3), or other viewing port device in the viewing port filter plate retaining mechanism. The mounting mechanism may be specially designed for a special viewing port device or it may be somewhat universal being able to mount a variety of different types of viewing port devices in the viewing port filter plate retaining mechanism 14 (sometimes referred to herein as a mounting structure) of the welding helmet 10.

The lens in the viewing port, sometimes referred to simply as the viewing port itself, may be a dark filter plate of glass or other material. The viewing port 12 may be a welding lens that automatically darkens or lightens, for example, as is described in the above-mentioned patents. Such a welding lens can be part of a cartridge assembly secured by the retainer mechanism 14 as exemplified at 40 in FIG. 3. Other types of viewing port devices also may be used.

In using the welding helmet 10, a person would place the mounting headband onto the head and would pivot the shell 11 to a desired orientation either tilted up on top of the head or tilted down in front of the face. An exemplary mounting headband or head gear is shown schematically at 13b in FIG. 7. The welding helmet 10 provides protection for the eyes of the welder from the ultraviolet, visible and infrared light emitted during welding. The shell 11 and viewing port 12 also provide a measure of protection blocking from the face fumes, heat, hot metal spatter and sparks, and possibly other debris.

The material of which the frame 20 is made preferably is a thermoplastic. One exemplary thermoplastic material is polyamide (Nylon). Other thermoplastic materials include polycarbonate, polyester, polyethylene, polyphenylene sulfide, polyimide, polyurethane, ABS, etc.

Preferably the material of which the frame 20 is made is able to be molded, more preferably injection molded, and most preferably insert molded with the preformed composite panels placed in the mold prior to the injection of the thermoplastic resin material. Insert molding is a known technique and is used, for example, in the manufacturing of electrical connectors.

The material of which the composite material panel 21 is formed may be a woven fiber, such as that sold under the trademark Kevlar. Such woven fiber may be embedded in a resin matrix to form a single ply or a multiple ply (laminate) material. The composite material alternatively may be a carbon fiber material, a fiberglass material, or laminated hybrids of the various woven or non-woven materials available. The woven fiber material of which the composite material is formed preferably is provided in the form of a sheet of such material, and that sheet may be impregnated with epoxy, polyester resin, and/or other resin or other matrix material.

To make the shell 11 of the welding helmet 10, according to an embodiment of the invention, a woven sheet of Kevlar fiber material is impregnated with epoxy or polyester resin and/or other stiffening materials. The impregnated sheet material is pressed into the desired shape and is cured using conventional techniques, such as by elevating the temperature, applying a vacuum, and/or applying pressure. This technique may be used to form a single ply or a multiple ply wall panel for the helmet. The helmet 10 may include a plurality of such wall panels, each being formed in a particular shape to cooperate with respective portions of the frame material 20 with which they are to be interconnected as an integral structure.

Alternative processes by which panels of the composite material can be fabricated also exist. One example is known as resin transfer molding (sometimes referred to as RTM) in which resin is transferred or injected into a mold where the woven fiber already has been inserted or draped to form the shape of the particular panel or object. After the resin has been cured suitably, the panel or part can be removed. The resin preferably provides suitable stiffness for the composite material. The woven fiber can be supplied in a shape that is preformed to the shape of the part intended to be made or it may be manually laid up to form the structural shape of the part and then trimmed after curing to provide the final shape of the part or the panel being made.

The frame 20 is made of thermoplastic material, as was mentioned above. In an embodiment of the invention the frame 20 is made by an insert molding technique. The insert molding technique includes placing in a mold the panels of the already formed relatively stiff composite material 21. The mold then is closed, and the panels of the composite material are held in place by the mold parts. Thermoplastic material then is injected into the mold at specified locations to form the frame 20. More particularly, preferably the mold has spaces where the thermoplastic material will flow to form the back of the frame 20a, front 20b of the frame which provides the viewing port filter plate retainer mechanism 14, and ribs 20c of the frame. The various portions of the frame 20 are directly molded to the composite material panels to form an integral structure therewith.

Turning now to FIG. 3, an elevation view of the welding helmet 10 with the front face of the helmet in section is shown. The frame 20 is molded to and attached directly to respective panels 21 of composite material at the edges 50 of those panels. The junction 51 of the panels 21 and frame 20 is a lapped type of junction as is seen in FIG. 3 and in the enlarged section view of one of the junctions in FIG. 4. The edge 50 of the panel 21 may be relatively ragged. However, the lapping frame material 52 substantially encases the ragged edge and extends along a sufficient distance of encased composite panel material shown at 53 in FIG. 4 both to provide security and integrity of the connection of junction 51.

The frame 20 preferably is sufficiently stiff to provide structural rigidity to the welding helmet 10. Additionally, the frame 20 may have various mechanical details in it for securing the viewing port retaining mechanism 14 to the frame, such as by means of the above mentioned hinge points 34, latches, screws, and rivets, etc. The frame 20 also may have a mechanical detail in the form of holes or openings 55 for attaching the mounting headband to the welding helmet.

Figure 7:
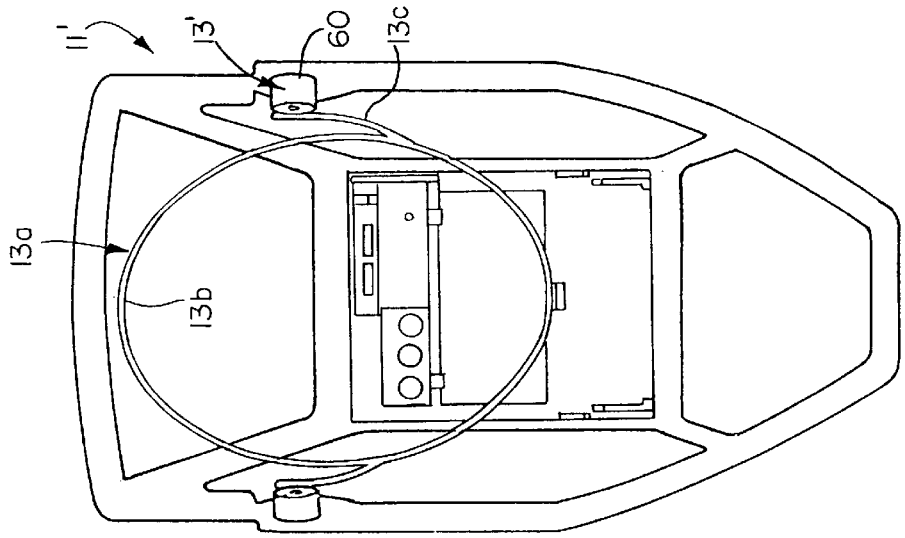
FIG. 7 is a back elevation view of the welding helmet of FIG. 5.
Figure 6:
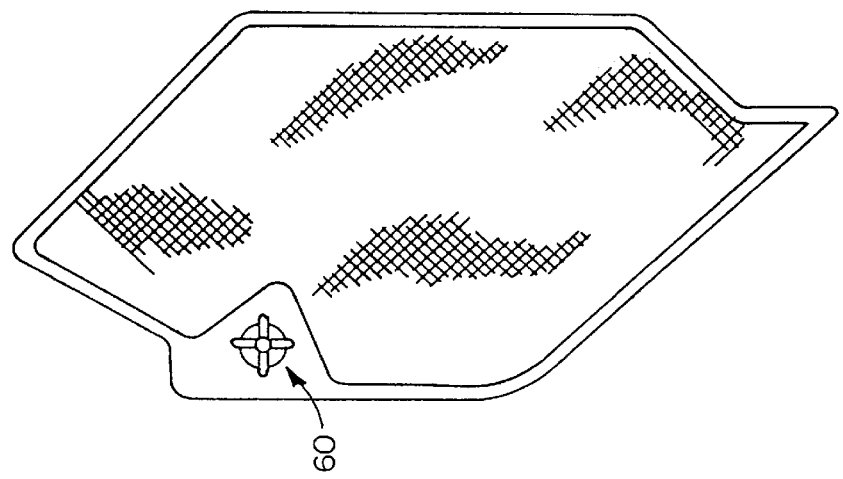
FIG. 6 is a side elevation view of the welding helmet of FIG. 5.
Figure 5:
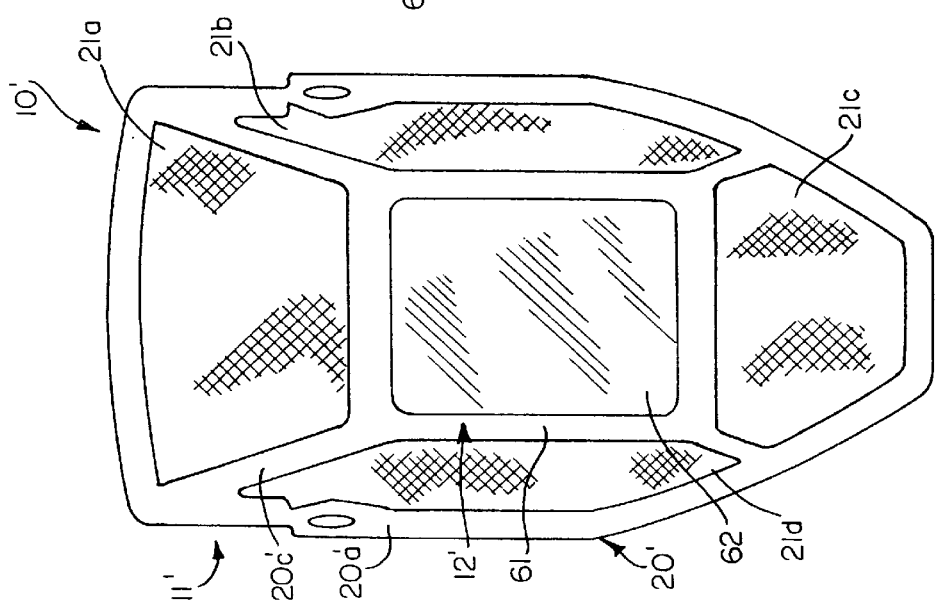
FIG. 5 is a front elevation view of another embodiment of welding helmet.

Referring to FIGS. 5–7, another embodiment of welding helmet 10' is shown. The welding helmet 10' is similar to the welding helmet 10. In FIGS. 5–7 primed reference numerals will be used to designate parts which correspond to parts in the welding helmet 10 of FIGS. 1–4 and are designated by unprimed reference numerals.

The welding helmet 10' includes an outside shell 11', a viewing port 12', head gear 13a in the form of a mounting strap 13b and a fastening strap 13c, which are connected at a pivot connection 13' to the shell 11'. A nut and bolt connection 60 seen in FIG. 7 attached the head gear 13a to the shell 11' in a conventional way.

Looking at FIG. 5, the frame 20' includes a front 61, which serves as the viewing port filter/coverplate 62 retainer. In this case it is not removable as is shown at 14 in FIGS. 1 and 2, but instead the filter and coverplate are held in place by a wire formed spring (not shown). In the welding helmet 10' an integrally formed viewing port 61 is shown with the coverplate 62 providing protection from scratching or the like is seen on the outside face thereof.

The frame 20' also includes a back frame structure 20a' and four web-like struts 20c'. Four composite panels 21a through 21d are adhered to and structurally supported by the frame 20 in the manner shown previously in FIG. 4.

The welding helmet 10' can be made using the methods described above.

Another method for making welding helmets in accordance with the present invention includes using as the composite material a material which is activated in response to the conditions that occur during the insert molding process. Therefore, the composite material may include a sheet of woven fiber material, such as Kevlar, that is impregnated or coated with a resin that melts and cures during the insert molding process and/or thereafter. For example, the sheet material is placed in the mold, and the mold is closed. The mold temperature is raised to melt the resin that is impregnating or coating the sheet material, and thermoplastic material is injected to the mold at the respective locations where the frame 20 is to be formed. After injection has taken place, the mold is cooled; alternatively, the mold can be opened and cooled. During the latter processes, the thermoplastic preferably has solidified or does solidify, and the resin associated with the sheet material also cures to a relatively stiff condition.

Alternatively to the above described methods, it is possible that the composite material and the frame material can be secured together using mechanical fasteners, by adhesive bonding using an adhesive material, by heat staking, and/or by ultrasonic welding techniques. Regardless of the technique used to secure the composite material and the frame material together, it is desirable that the two are secured sufficiently well to form an integral structure or a near integral structure whereby the frame material provides structural support for the composite material.

Various mechanical features may be included in the frame material. Examples include the mounting structure for the head gear described above. Another example of a mechanical feature is the hinges or locking mechanism used to secure the viewing port 12 and subsequent filter/coverplate retainer 14 in place in the frame. Other mechanical features include devices to attach a respiration hose and to provide light filtration components to the welding helmet, shell, or other device embodying the invention.

By using composite material which is relatively light weight compared to materials previously used for welding helmets, and especially by using a frame material to provide a structural support for the composite material, the overall weight of the welding helmet 10 can be reduced compared to prior welding helmets that provided similar types of protective functions for a welder. Additionally, the welding helmet according to the invention has high temperature resistance, for example, being particularly resistant to hot metal spatter or sparks, as well as to fumes and heat generated by a welding arc due to the characteristics of the composite material and the integral connection between the composite material and the frame. Furthermore, due to the characteristics of the composite material and the cooperative structural support provided the composite material by the frame, the welding helmet has good durability being able to withstand relatively severe impacts. Thus, the overall strength of the welding helmet per volume of material required to make the welding helmet is greater than that of prior art welding helmets. By providing such strength characteristics and minimal material requirements, the weight of the welding helmet can be reduced.

Referring, now, to FIGS. 8–19, there is illustrated another embodiment of welding helmet 110 in accordance with the invention wherein the shell 111 of the welding helmet is made of preferably a single sheet of composite material. In FIGS. 8–13 parts which are similar to parts described above that are designated by reference numerals 10 through 99 are designated by the same reference numerals plus 100. Thus, welding helmet 110 is similar to welding helmet 10, and the differences between the two welding helmets are described below. This convention facilitates description of the welding helmet 110 without the need to repeat previous description relating to the earlier described similar part.

The helmet 110 includes a shell 111 and a viewing port 112. Headband pivot connection pivot holes 113a are in side walls of the shell 111. The viewing port 112 is located in the front 115 of the helmet and the back 116 of the helmet is open to receive the face of a person (welder). A mounting headband (not shown) may be attached to the shell 111 at the pivot holes 113a in the manner described above with respect to the mounting head band or head gear 13b in FIG. 7.

The helmet shell 111 is a composite material 121. In the illustrated embodiment the composite material is woven Kevlar fiber, fabric or cloth material, and that material is coated, embedded with, otherwise containing a resin. Other exemplary composite materials which may be used in the invention include fiberglass material, carbon/graphite material, or a blend of two or more of these materials or of one of these materials and another material woven into a cloth or fabric. Fiberglass material may be laid up and/or otherwise molded. An appropriate resin or the like also would be included as with the Kevlar and other materials.

Other materials which can be molded in accordance with the invention and which provide suitable strength, durability, fire retarding, and like characteristics also may be used. In an embodiment the helmet may be made by injection molding a plastic molding material.

The composite material includes resin. An example of a method for making Kevlar (or other) composite material is referred to as a "prepreg" process. The prepreg process starts with the woven fabric, impregnates the fabric with a liquid resin mix, dries off some of the volatiles and freezes the fabric. The freezing slows the cure time so that the fabric can be shipped and subsequently used. Exemplary prepreg materials are mentioned below.

The resin may be a variety of materials including a broad range of epoxies and other adhesives. For a welding helmet application desirable properties include very high temperature resistance, somewhat fast cure time, ability to modify the properties by adding doping materials, bonds well with Kevlar, carbon/graphite and/or fiberglass material and a reasonable cost. The family of resins known as phenolic resins is particularly suitable, although other materials show similar features and capabilities and may be used. Phenolic resins are available from a variety of sources including Georgia Pacific. Exemplary phenolic resins and phenolic molding compounds are sold under the designation ICI Fiberite Molding Materials by ICI Composites Inc. of Winona, Minn. One of many examples is presented below.

Exemplary dopants or additives to the resin system that can improve the features of a standard phenolic resin system include:

1. Carbon: Adding carbon or other light blocking of colored components is useful to change the color or tone of the phenolic resin from a neutral or transparent color to a black or light blocking color. This step eliminates the need to paint the final helmet shell and adds design appeal. The carbon does not affect the phenolic material or the bond thereof to the Kevlar material. Standard carbon black dispersions are available from a variety of manufactures. The content may be from 0.1% to 1.5% carbon by weight of phenolic material (and other additives). Dye also or alternatively may be used, if desired.

2. Rubberizing Agent: Many standard phenolic resin systems are very hard and brittle when fully cured. Adding a small amount of rubberizing agent to the resin (such as 0% to 10% by weight) will increase the flexibility.

Adding too much rubberizing agent (over about 10%) will tend to reduce the heat and flame resistant properties. Exemplary rubberizing agents include rubber dopants, such as B-90 Butyl Rubber, available from Monsanto.

3. Flame retardant: Standard flame retardant chemicals may be used in a variety of prepreg composite material designs and, if desired, also may be used in the present invention. However, Kevlar composite material usually does not burn or does not burn very well; and, therefore, the use of a flame retardant may be unnecessary.

A exemplary Kevlar material weave pattern is a satin weave or comparable weave that has high conformity to draping over complex shapes. However, a "plain" weave or other weaves can also be used provided the weave is suitable for molding. An exemplary thickness of the cloth material is from about 0.015 inch to about 0.100 inch. The woven composite fabric or cloth is available from a number of sources including ICI Fiberite of Tucson, Ariz., Hexcel Corporation of Dublin, Calif., BGF Industries, Inc. of Greensboro, N.C. and others. An example of Kevlar material sold by Hexcel Corporation under the category Advanced Composite Fabrics and which is useful in the invention is, as follows:

Kevlar 49-500. This material has a 5 H-Satin weave, 13.0 Mils thickness, yarn type K49/2160 DN warp and fill, 17×17 count, 9.00 oz./yard$^2$, and breaking strength of 920 lbs./inch warp and 970 lbs./inch fill.

Preferably the composite material 121 is a single sheet of such material which is molded to the shape of the welding helmet 110, as will be described in detail below. Alternatively, the composite material may be several sheets of composite material which are made essentially integral either before or during the molding process, although this may be less desirable than a single sheet composite material because there may be some weaknesses at a seam where the composite material sheets are joined.

Preferably the composite material 121 is a single layer sheet and is not a plurality of layers, such as is used in body armor, steering fins for rockets, and the like. The single layer is light weight and has sufficient strength and integrity to provide the desired protection for the welder. For example, the Kevlar material used in the invention may be a relatively thick weave of the Kevlar fiber material. Such a Kevlar material weave sometimes is referred to as "ballistic cloth." The composite material is molded to shape forming the shell 111 of the welding helmet and such shell provides protection for the welder. Also, a single sheet is easier to cut to place in a mold or to turn after molding, compared to a multiple sheet thickness.

The composite material 121 is molded to the shape of the shell 111 of the welding helmet 110, as will be described below. The composite material 121 of the type described already impregnated with the carbon and phenolic resin material is a thermoset material and has been found to cure in response to suitable temperature conditions relatively expediently. The cure time can be determined by the particular ingredients of the composite material and the molding conditions, such as those described below. Curing may refer to a cross linking process or to some other process by which the composite material is hardened and/or stiffened to retain its shape, as is well known.

Consistent with the invention, other composite materials may be used for the welding helmet 110 shell 111. Such other material should have the desired strength, stiffness, impact resistance, flame retardance, rigidity and durability. The Kevlar composite material 121 of the type described above stops penetration of welding material or other materials. In one embodiment it meets the ANSI high mass impact test, which sometimes is referred to as the ANSI C87 standard. According to such standard, a weight of 500 grams generally in the shape of a pointed bullet is dropped from 4 feet to impact the material being tested. To meet the requirements of that drop test, the bullet-shape weight cannot penetrate the material.

In an embodiment the helmet 110 blocks light transmission and also desirably blocks spatter that occurs during welding from reaching the welder's face.

In an embodiment the carbon in the composite material 121 blocks light sufficiently to eliminate the need for painting or for dye to absorb light. In such embodiment the composite material is impregnated with carbon, graphite or the like in the phenolic material to make the helmet black to block light transmission other than where the viewing port 112 is located. However, if desired, the shell 111 of the welding helmet 110 may be painted or may include dye for the purpose of reducing light transmission therethrough.

The flame retardant, if used, in the composite material 121 can help to prevent the welding helmet from catching fire or burning when a spark or piece of hot metal or welding material impinges thereon.

The Kevlar composite material 121 is relatively easily frayed at the edges thereof. Therefore, a trim or rim 201 is placed about the edge 202 (FIGS. 9, 11, 13 and 15–18) at the viewing port 112 in the front 115 of the welding helmet and a trim or rim 203 is placed about the edge 204 (FIGS. 9–12, 14, 15, 17 and 19) at the back 116 of the welding helmet. The trim pieces 201, 203 may provide both protection for the edges 202, 204 to avoid fraying or other damage thereto and also may provide stiffening or rigidifying function for the shell 111 of the welding helmet 110. Thus, the trim pieces 201, 203 are similar in function to the frame portions 20a, 20b described above.

The trim pieces 201, 203 may be molded plastic shaped as shown to conform generally to the shape of the shell 111 edges 202, 204. The trim pieces may be plastic, rubber, metal, or some other material. The trim pieces 201, 203 may be attached to the shell 111 by adhesive material, by force fit, by ultrasonic welding, by melt/ultrasonic staking, etc., or by any other method. Each trim piece 201, 203 may be one piece or formed of plural pieces, which are fastened to each other at or through the composite material at or near the respective edges 202, 204 being protected.

The trim 201 at the viewing port 112 also is part of a mounting structure 205 to hold a welding lens cartridge assembly 140 (FIG. 17) for the helmet 110 in the shell 111.

The mounting structure 205 mounts the welding lens cartridge assembly 140 or some other lens, light, automatic darkening welding filter, etc. in the viewing port 112 area of the welding helmet 110 shell 111. Another exemplary mounting for the welding lens cartridge 140 is illustrated and described with respect to the opening 33 and retainer mechanism 14 in FIGS. 1–7 and may be used in the welding helmet 110.

The piece 201 may be formed of two pieces, which are shown in FIGS. 17, 18 and 20–26. The trim 201 in combination with a spring 206 (or other retainer) also serves as the mounting structure 205. The welding lens cartridge assembly 140 may be of the type that includes an automatically darkening welding lens, such as those disclosed in one or more of U.S. Pat. Nos. 4,039,254, 4,039,803, 4,237,557, 5,074,647, 5,208,688 and/or 5,377,032. Alternatively, the welding lens cartridge assembly may be a nonchanging filter, such as dark glass, an infrared filter, an ultraviolet filter, a clear glass, a combination thereof, or any other means through which it is possible to view a welding operation or the like while providing protection for the eyes of the viewer, e.g., mechanical protection and/or visual protection.

As is illustrated in FIGS. 17, 18 and 20–26, the trim 201 of the mounting structure 205 includes an annular face part 210 and an annular mounting part 211, which can be sandwiched together at the viewing port 112 of the shell 111 in the manner illustrated. In sandwiching the parts 210, 211, they preferably cover the edge 202 of the viewing port 112 to provide protection thereof from fraying and to provide an aesthetically clean or finished appearance and leave an open area 212a at the center thereof for viewing via the welding lens. The annular face part 210 includes an annular flange 213, which has a smooth front surface to provide a finished clean appearance and a back surface 214 to engage the composite material at the area of the edge 202. The annular face part 210 also has a mounting rim 215 which is substantially circumferentially about the opening 212b and is of a depth that preferably is sufficient to extend beyond the thickness of the composite material 121 at the viewing port 112 to engage the annular mounting part 211 and to fasten thereto. Alternatively, the annular mounting part 211 may include a means, such as the rim 215 or some other part to attach to the annular face part 210. Other means also may be used to secure together the annular face part 210 and the annular mounting part 211 of the trim piece 201.

The annular mounting part 211 includes a rectangular frame-like structure 220 having a front surface 221 that preferably engages a surface of the composite material 121 and a back surface 222. The front surface 221 and the confronting back surface 213 of the annular face part 210 provide a sandwich-like structure with the edge 202 of the composite material 121 therebetween, and preferably is securely resiliently engaged therewith so the trim 201 is relatively fixedly held to the composite material 121.

The frame 220 has a stepped recess 223 about the inner perimeter thereof to receive therein the mounting rim 215 of the annular face part 210. Preferably part of the rim 215 snaps resiliently into the recess 223 temporarily to hold the two parts together. With the mounting rim 215 so located in the recess 223, the two parts 210, 211 may be secured together by ultrasonic welding. If desired the two parts 210, 211 may be secured by adhesive material, by staking, by other fasteners, or the like, or a combination thereof.

A welding lens cartridge assembly 140 can be mounted and held by the spring 206 of the mounting structure 205 against the trim 201. Several slots 232 in the top of the mounting part 211 receive tab-like protrusions 233 at the top of the spring 206 and retain those protrusions therein, and several locking tabs 234 engage a bottom portion of the spring to retain the spring in place against the locking tabs. The spring 206 is made of wire, although it may be of plastic or other material, which has sufficient resiliency to be deformed slightly while being held in place by the slots 232 and locking tabs 234 to provide a force against the welding lens cartridge assembly 140 holding it in place against the mounting part 211 of the trim 201.

The annular face part 210 and annular mounting part 211 may be made of plastic and may be formed by injection molding or may be made of other material and/or by other processes. The actual size and shape of the parts 210, 211, should be suitable to fit in the area of the viewing port 112 engaged with the edge 202 of the welding helmet shell 111. The actual size of the openings 12a, 12b in the respective parts 210 and 211 are selected to provide the desired viewing function for the welding helmet, to accommodate the size and shape of the welding lens cartridge assembly, etc.

The trim 203 is shown in partial section view in FIG. 19. The trim 203 may be rubber, plastic, or other material, extruded or otherwise formed in the shape of an elongate body of a length to extend along a desired extent of the edge 204, e.g., along the entire length thereof at the back 116 of the welding helmet 110. As is seen in FIG. 19, the trim 203 is an elongate member of U-shape cross section. The portion of the shell 111 composite material 121 adjacent the edge 204 fits into the slot 240 between the legs 241 of the "U" to mount the trim 203 on the shell material. Adhesive material or some other material or technique may be used to secure the trim 203 to the shell. If desired, the trim may be molded directly to the composite material.

A trim piece (not illustrated) may be used at the holes 113a to provide protection of the edges and to provide reinforcement and/or stiffening function for the mounting structure for the headband/headgear.

The molded composite material 121 tends to be relatively stiff after curing so that it tends to retain its shape as a welding helmet. The trim pieces 201, 203 also add stiffness around the edges 202, 204. For example, the trim pieces 201, 203 can be useful to hold shape and to support the composite material 121 when struck hard to avoid deformation of the composite material, e.g., if hit by a tool or dropped onto the floor. The trim pieces also may provide strength and durability. For example, if the trim 203 is rubber, it may absorb shock force if the helmet 110 is dropped.

In the past stiffness was expected of the helmet material before it was finished. In the present invention there is some flexibility until the center frame structure or trim 201 and the outer trim 203 are attached. Thereafter, the molded composite material and .trim pieces may cooperate to increase stiffness and rigidity for the welding helmet 110. Stiffness of the welding helmet 110 also is provided by the cured composite material itself.

Although the welding helmet has adequate stiffness or rigidity to maintain shape and to provide protection from spatter and small particles for the face and/or head of the welder when used during welding, preferably the welding helmet has a degree of flexibility. Such flexibility adds to durability characteristics of the welding helmet, for example, if the helmet were dropped, allowing the helmet to flex or to deform somewhat in order to absorb the shock of the fall and hitting the ground/floor. Suitable flexibility also may enhance other durability features of the welding helmet and may facilitate storage in boxes, in stacked relation or in some other fashion. A rubberizer may be added in the resin/phenolic material of the composite material 121 for increasing flexibility.

Another feature of the welding helmet 110 of the invention is the use of a number of crimps, bends and/or folds in the composite material 121 of the shell to facilitate molding as a one piece shell and to contribute to stiffening. Exemplary curved steps 250 at the sides 251 of the welding helmet 110 provide such stiffening function and also may contribute to aesthetics. Similar steps 252, 253 in the respective top 254 and bottom 255 portions of the welding helmet shell 111 also provide such stiffening function and may contribute to aesthetics. The curvature of the step 250 where the composite material goes from the area, curved plane or surface 256 that is approximately at one spacing outward from the center of the interior of the welding helmet to the area, curved plane or surface 257 which is relatively recessed and, therefore, somewhat closer to the center of the helmet interior also may contribute to such stiffening function. Stiffening also may be similarly provided by curvature of the steps 252, 253 in the front (top and bottom) of the welding helmet.

In the past it has been difficult to mold composite material made from woven Kevlar fiber that has sufficient strength and durability characteristics which would be suitable for a welding helmet. A feature of the welding helmet 110 of the invention is the use of relatively gradual and to a large extent substantially unidirectional curves, e.g., as in a cylinder, at various portions of the welding helmet and the minimizing of multidirectional curves, e.g., as in a sphere or part of a sphere. The shape of the curves allows the composite material to be draped in the molding and pre-molding equipment during manufacturing of the welding helmet 110 so as to avoid wrinkles in the material and binding of the material in the mold. Drapability of the fabric also depends on the weave of the material. The more drapable the weave, the sharper the curve possible. In any case, the curves preferably are gradual compared to sharp corners.

An example of such curves is illustrated at 260, 261 along respective junctions between the sides 251 and the front 115 of the welding helmet. Each of the junctions 260, 261 follows a three dimensional contour to provide depth for the welding helmet between the front 115 and back 116. For example, as is viewed in FIG. 10, the top portion 261a of the junction 261 extends in a somewhat horizontal direction between the back and front of the welding helmet shell 111; a predominantly vertical section 261b extends between the top and bottom of the welding helmet; and a bottom section 261c is directed again somewhat toward the back of the helmet.

Portions of the junctions 260, 261 also are somewhat rolled or cylinder-like. What is meant by "rolled" is the following. Assume that there is an axis of the junction 261 extending from the top, along the front, and to the bottom of the welding helmet as it is viewed in FIG. 10, for example, generally following the portions 261a, 261b, 261c . Such axis is schematically represented in FIG. 10 by the phantom line 262. The material of which the junction 261, for example, is formed, is rolled or otherwise somewhat curved about the axis 262. An effort to depict such rolled curvature is illustrated in a number of the drawing figures hereof and is especially evident in top views of FIGS. 14 and 15. Such rolled curvature facilitates molding the composite material as a one piece shell 111 and also helps to provide stiffening function described herein.

As is seen in the section view of FIGS. 11–15, the results of such rolling of the composite material at the junctions 261a, 261b in the front 115 of the helmet shell 111 is the relative recessing of the edges 202 of the viewing port 112 compared to the relatively raised surfaces of the junctions 260, 261. This recessing allows for a smooth flowing of the composite material at the junctions material 260, 261. The curved junctions enhance stiffness, strength and durability for the welding helmet and the recessing protects the welding lens from damage in the event the welding helmet is placed front first against a surface, such as the floor. A similar curvature of the composite material also is seen in FIG. 9 from the area 254a at the top front 254 of the welding helmet and at 255a at the bottom front. Such recessing and curvature of the composite material at the top front 254 and bottom front 255 of the welding helmet shell 111 provide stiffness function and also may contribute to protection of the lens and to aesthetics of the welding helmet.

Another feature of the invention, which is illustrated in enlargement in FIGS. 11 and 13–16 is a thickening of the wall of the shell 111 at the areas 202a, 202b, 202c of the edge 202 circumscribing the viewing port 112 relative to other less thick portions of the shell. Such relatively thickened wall portion can be formed during the process of molding the composite material 121 to form the shell 111. The thickened portion of composite material at the edge area 202 increases the strength and stiffness of the material there. The areas 202a, 202b also increase the amount of material able to grasped securely between the annular flange 212 and the surface 221 of the parts 210, 211. The thicker material at the edge areas 202a, 202b helps to assure that the trim 201 will attach securely to and accurately positioned on the shell.

Although the thickened portion of the edge 202 may be provided by the molding technique with which the shell 111 is formed of the composite material 121, alternate means may be used to provide the thickened material. For example, an additional layer of resin, adhesive, or other material may be applied to the composite material in the areas 202a, 202b, 202c of the edge.

In an embodiment of the invention, the approximate average wall thickness of the composite material is on the order of 0.060 inch, and the approximate thickness of the thickened wall sections 202a, 202b is on the order of approximately 0.090 inch. Other thicknesses may be used consistent with the invention.

As is described below, molding in accordance with the present invention includes the placing of the composite material for the shell 111 into a mold and shaping it. Ordinarily it is not necessary to inject any material into the mold, such as by plastic injection molding technique or some other technique. Since there is no injection of material, the need to cause material to flow together in a mold is unnecessary. Such flowing of material in a mold may result in knit lines, for example, where material flowing in opposite directions comes together and "knits". Sometimes knit lines are a place where weakness may occur in a device. Accordingly, such weaknesses are not encountered in the molded one piece helmet 110 embodiment of the invention.

Figure 27:
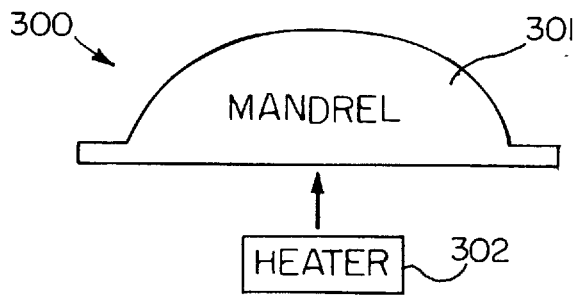
FIG. 27 is a schematic illustration of the mandrel portion of the molding apparatus for making a welding helmet in accordance with an embodiment of the invention.

In manufacturing the welding helmet 110 a two step molding process preferably is used. One step in the process is to preform the composite material generally in the shape of a mold and the second step is to effect the molding in such a mold. The preforming may be carried out using a mandrel or some other type of pre-molding machine 300, as is represented in FIG. 27. The actual accurate molding (or second step of the process) may be carried out in a compression type mold in which there is a hollow mold cavity that is of a shape corresponding to the desired shape of the welding helmet.

Since Kevlar material typically has been relatively difficult to mold, it has been found that using the two step molding process enables the Kevlar material to be molded to the desired shape of the welding helmet having the various intricacies of steps, curves and bends described and illustrated. The premolding step preliminarily shapes the composite material approximately to the shape of the primary mold to facilitate fitting in that mold and substantially fully filling out the primary mold in response to applied pressure as is described below. An exemplary molding system and method in accordance with an embodiment of the invention is described below. It will be appreciated that other or additional techniques may be used to make the molding helmet 110 in accordance with the invention.

Turning to FIG. 27, a mandrel pre-molding machine 300 is shown. The mandrel pre-molding machine 300 includes a mandrel 301 having a desired shape that somewhat approximates the shape of the mold and of the welding helmet 110. The mandrel 301 may be a metal form onto which the uncured composite material 121 is placed. The composite material, for example, the above pre-preg material, is urged manually and/or by a tool into engagement with the mandrel 301 to take on the shape thereof, e.g., a somewhat curved shape rather than flat or planar shape of the unshaped composite material. The mandrel (and/or the tool if used) may be heated by a heater 302 to facilitate urging the composite material into the shape thereof; however, since the composite material preferably is a thermoset material the elevated temperature should be inadequate to cause relatively rapid curing or even any curing.

The mandrel can be simply a male casting that is the shape of the inside of the welding helmet. The shape of the mandrel preferably approximates the shape of the finished helmet. This is used for rough preforming of the composite fabric by pulling the fabric down into a "draped" position. The preshaped form, i.e., the preshaped fabric, can then be quickly loaded into the compression mold with reduced risk of wrinkles or other alignment problems.

Figure 28:
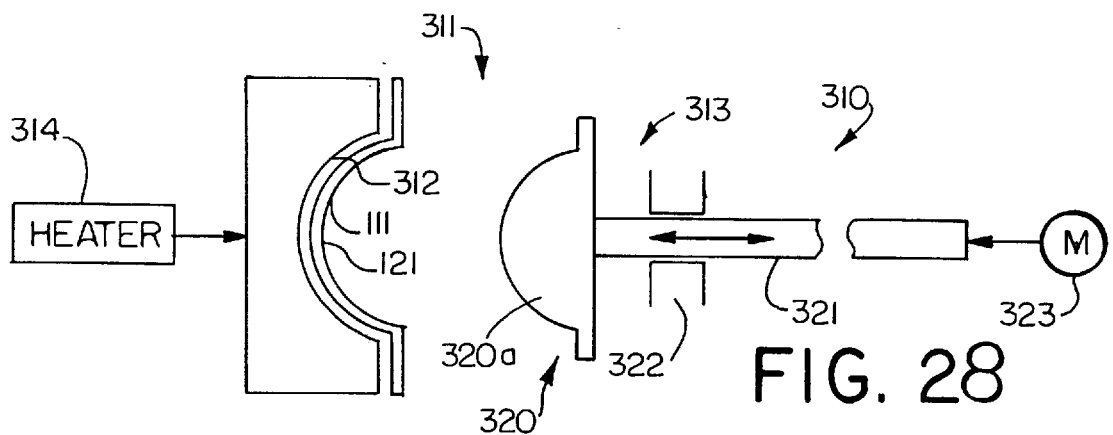
FIGS. 28 and 29, are, respectively, schematic side elevation views of a compression molding apparatus, respectively in open and closed condition.
Figure 29:
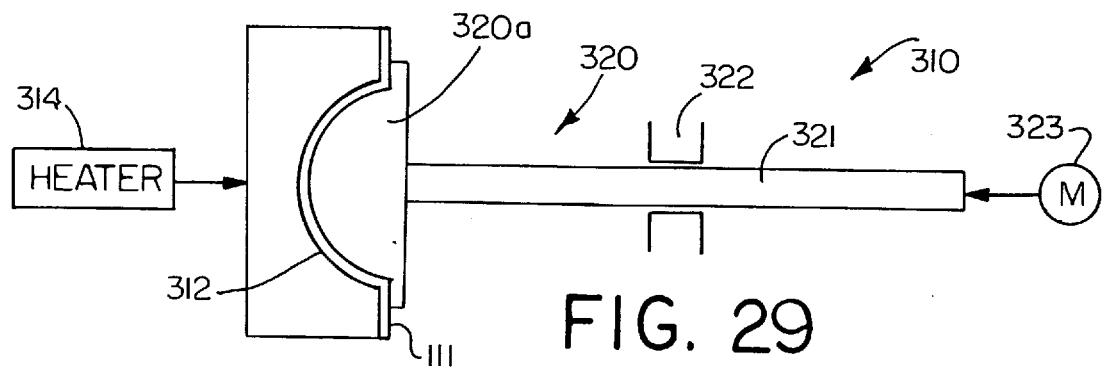

A compression type molding machine 310 (sometimes referred to as a compression press) shown in FIGS. 28 and 29 includes a mold 311, having a mold surface 312 in the shape of the final molded welding helmet shell 111, and a compression mechanism 313 which urges the composite material 121 into the mold 311 into close engagement with the mold surface 312 to shape the composite material in the desired shape of the final molded welding helmet shell. The mold 311 preferably is heated by a heater 314 to heat the composite material 121 during molding in order to cause and/or to expedite curing of the thermoset material, for example, the phenolic resin, thereof. If the composite material is able to cure without heating, such heater may be eliminated. Alternatively, if curing of the composite material can be effected and/or facilitated by applying a catalyst or other ingredient thereto, means may be provided in the mold to supply such catalyst or other ingredient before or while the composite material is in the mold. Other means to cure the composite material also may be used.

The compression mechanism 313 includes a plunger-like device 320 generally in the shape of the mold surface 312. The plunger-like device 320 is intended to urge the composite material into the mold into close abutting engagement with the mold surface 312 preferably so that substantially all of the composite material engages the mold surface thereby to be molded to the shape of the mold surface. In the illustrated embodiment the plunger-like device 320 is a bladder 320a into which a fluid, such as air or liquid, may be placed. The shape of the bladder is the same or approximately the same as that of the mold surface 312 (or some other desired shape) and the bladder is somewhat flexible and/or resilient to facilitate conforming to the mold surface as the bladder urges the composite material into engagement with the mold surface. Appropriate features may be provided in the mold surface 312 and/or in the bladder 320 to form the curves, steps, thickened areas, e.g., 202a, 202b, 202c, as may be needed.

The air bag or bladder should be in the shape of the mold effectively to urge the cloth against all desired surfaces of the mold. Thus, the mold preferably is solid material, e.g., aluminum, steel or some other material; the air bag/bladder may be a rubber material. Preferably the air bag/bladder has some flexibility so that it fits into close engagement with the various shapes of the mold. The air bag/bladder may be a rigid material; but that would require further precision forming of it for proper fit with respect to the mold. However, by using a somewhat flexible material it is less expensive because such precision manufacturing is not required and it also able to accommodate variations in thickness of the cloth.

The plunger-like device 320 is mounted on a support rod 321 or other device which is mounted in a bearing 322 and is moved by a motor 323 or other device toward and away from the mold. The plunger-like device 320 may be heated to provide an additional source of heat for curing or to assist in curing the composite material. If desired, the plunger-like device 320 may be heated by heating the fluid therein or by some other means. Such compression molding machines are commercially available, although the particular mold and mold surface 312 are novel and are configured to the desired shape of the welding helmet.

Other compression molding machines are available to mold the helmet shell 111.

In molding the helmet shell 111 of composite material 121, molding can be carried out in about ten minutes. If several, for example, five, molding machines are run simultaneously, and are offset in sequentially timed operation, that would permit one helmet shell to be molded completely every two minutes with relatively minimal manual operation. This is relatively high speed production and can be accomplished because of the relative simplicity of the shell material itself, e.g., it is a single sheet, single layer material, and because of the techniques described herein to mold a composite material shell.

According to the invention, the welding helmet 110 is manufactured by molding the entire composite material as a formed sheet. Then the trim pieces 201, 203 are attached about the outside edge and about the inside edge of the viewing port, the head gear is attached, and the welding lens cartridge assembly is mounted by the mounting structure.

Summarizing the method steps, a. Use as the composite material 121 raw Kevlar woven cloth already impregnated with carbon, phenolic and flame retardant.

b. Cut the cloth to shape to fit the mandrel and the mold surface.

c. Pre-form the cloth by placing it over a mandrel and applying heat from a heat gun or blower to generally shape the cloth to approximately the shape of the mold.

d. Place the pre-formed cloth into the mold.

e. Using an air bag/bladder, force the cloth into the mold into engagement with the mold surfaces.

f. Apply heat and continued pressure to the cloth by heating the mold (hot tool) and/or the bladder to cure the composite material and urging the cloth by the bladder into close engagement with the mold surface of the mold.

g. Open the mold.

h. Remove from the mold the formed composite material as the shell 111 for the welding helmet 110.

i. Trim the edges, such as edges 204, for example, the edges about the opening 113*a*, etc., of the composite material for accurate desired shape. Since it is only a single layer, it is easy to trim. Trimming the edges may be by a die cutting machine, by a knife or scissors, or by some other means. The viewing port 112 also may be cut at this point in the process. Cutting of the viewing port may be performed by a die cutting machine, knife, scissors, or by some other means.

j. Attach the trim 201 at the viewing port 112 edges 202 and the trim 203 around the back edges 204. The trim pieces can be applied by hand or extruded directly to the edges of the composite material.

k. Mount the welding lens or other device in the viewing port 112.

The above steps are exemplary of a method in accordance with the present invention. Several of the steps may be eliminated, depending on the type of material, mold, shape of device, etc. being manufactured; and additional steps may be added, as will become apparent to those having ordinary skill in the molding and fabricating arts.

Prior devices using Kevlar, for example, were formed in multiple layers which were laid up in a mold to make a particular shape. This is time consuming and expensive. In the present invention, though, the composite material is molded as a single piece. Since Kevlar and other composite materials are not easily molded, the invention preforms the composite material using the mandrel and heat so the preformed material is generally in the shape of the mold. Then, the preformed material is placed in the mold and can be molded relatively accurately to the shape defined by the mold.

Also, to facilitate or to enable molding of the composite materials, the various curves of the shape of the helmet are such that they facilitate draping the material without wrinkles or binding. For example, such curves may be largely cylindrical, e.g., uniaxial, rather than multidirectional, e.g., spherical. Therefore, the composite material will follow the shape of the mold and does not have to yield so much to follow more complex multidirectional shapes.

The particular weave and thickness of the composite material are selected to get strength characteristics, to enable molding, and to facilitate draping as is described above. Some weaves are not symmetrical and they drape better in one direction than another. Therefore, an optimizing technique according to the invention is to orient the woven material so that the draping characteristics are aligned in a complimentary fashion to the design characteristics of the mold.

Using a weave structure for the composite material is preferred because the structured interlocking of the fibers provides strength as compared to a matted fiber and resin structure (such as typical fiberglass). By using a woven structure, a much smaller volume of material can be used to meet the strength requirements of a welding helmet. Less volume of material means less weight, which is especially advantageous in a welding helmet. Virtually any of the popular weave types may be used for molding the helmet. However, choosing a material with a weave pattern that has good draping characteristics (such as a satin weave Kevlar material compared to a plain weave) allows a design with a tighter radius on the complex curved surfaces of the welding helmet. Using a heavier weave material (normally 0.020" thick vs. 0.012" thick) increases the impact resistance of the helmet and increases its rigidity. Using a thicker fabric and weave structure and using it as a single layer formed product is advantageous to obtain the features described herein at reasonable cost. The phenolic resin increases the effective thickness of the composite material.

Many prepreg materials useful in the invention are available. Examples include ICI Fiberite models MX-82031, MX82029, MX-4949, etc. Some phenolic systems for prepreg materials useful in the invention include those sold by SP Systems under the designation Montecatini Advanced Materials, and particular prepreg materials from SP Systems include those designated CPH 2251 and Pyropreg AC.

INDUSTRIAL APPLICATION

It will be appreciated that the welding helmet of the invention is useful to protect welders from the hazards of bright light, heat and impacts, and the light weight characteristic of the helmet facilitates balancing on the head, provides improved comfort and fatigue. The features of the invention described may be used in various applications other than welding helmets, as is expressed above.

The embodiments of the invention claimed are, as follows:

1. A welding helmet comprising,
    a composite material molded to the desired shape of the shell of the helmet, and
    a viewing port in the composite material shell at the front,
    the viewing port including stiffening material relatively stiffer than the composite material and
    including a mounting structure for a viewing device through which light may be transmitted for viewing.

2. The welding helmet of claim 1, wherein the composite material comprises a woven material and hardenable resin.

3. The welding helmet of claim 1, wherein the composite material comprises a fabric material that consists of a single sheet.

4. The welding helmet of claim 1, wherein the composite material comprises para-aramid fiber material.

5. The welding helmet of claim 1, wherein the composite material comprises woven para-aramid fiber fabric and a curable resin.

6. The welding helmet of claim 1, wherein the composite material comprises woven para-aramid fiber fabric and a phenolic thermoset resin.

7. The welding helmet of claim 6, wherein carbon black material is included in the resin for blocking light transmission.

8. The welding helmet of claim 7, wherein a flame retardant is included in the resin.

9. The welding helmet of claim 1, wherein the composite material comprises a single sheet of woven para-aramid fiber fabric.

10. The welding helmet of claim 1, wherein the composite material comprises a graphite material.

11. The welding helmet of claim 1, wherein the composite material comprises carbon material.

12. The welding helmet of claim 1, wherein the composite material comprises fiberglass material.

13. The welding helmet of claim 12, wherein the composite material comprises woven fiberglass fabric and a hardenable resin.

14. The welding helmet of claim 1, wherein the mounting structure comprises outer and inner rims secured together and sandwiching and edge portion of the shell therebetween.

15. The welding helmet of claim 14, wherein the edge portion of the shell is thicker than the major extent of the shell.

16. The welding helmet of claim 14, wherein the inner rim includes a portion for engaging a welding lens assembly.

17. The welding helmet of claim 14, further comprising a member for holding the welding lens assembly to the inner rim.

18. The welding helmet of claim 17, said member comprising a spring.

19. The welding helmet of claim 14, wherein one of said rims includes a mounting rim and the other of said rims includes a mounting recess for receiving the mounting rim and connecting therewith to attach said rims together.

20. The welding helmet of claim 19, wherein said rims are ultrasonically welded together.

21. The welding helmet of claim 1, further comprising a welding lens assembly mounted in the viewing port as said viewing device.

22. The welding helmet of claim 21, said welding lens assembly comprising an automatically darkening welding lens.

23. The welding helmet of claim 1, further comprising a trim about the external perimeter edge of the shell.

24. The welding helmet of claim 23, wherein said trim comprises a resilient material.

25. The welding helmet of claim 24, wherein said trim comprises rubber.

26. The welding helmet of claim 23, wherein said trim adds stiffness to the shell.

27. The welding helmet of claim 23, wherein said trim is stiffer than the composite material.

28. The welding helmet of claim 1, wherein the shell is formed by compression molding.

29. The welding helmet of claim 1, wherein the shell is formed in a multiple step process, one step comprising compression molding, and another step comprising prior to compression molding preliminarily pre-shaping the composite material generally in the shape of the compression mold.

30. The welding helmet of claim 29, wherein the preliminary pre-shaping comprises draping the composite material over a mandrel-like device.

31. The welding helmet of claim 28, wherein the composite material comprises thermoset material and including the step of applying heat to the thermoset material during molding.

32. The welding helmet of claim 1, said shell comprising a plurality of relatively raised and relatively recessed portions coupled at respective steps.

33. The welding helmet of claim 32, wherein said steps increase stiffness of the shell.

34. The welding helmet of claim 32, a plurality of said steps traversing a curved path along the intersection thereof with respective relatively raised and relatively recessed portions.

35. The welding helmet of claim 34, further comprising a pair of roll-curved portions extending generally between the front of the shell and a respective side.

36. The welding helmet of claim 35, said roll-curved portions being of generally curved cross-section about a respective axis extending from a top portion and down across a front portion of the shell.

37. The welding helmet of claim 1, further comprising a pair of roll-curved portions extending generally between the front of the shell and a respective side.

38. The welding helmet of claim 37, said roll-curved portions being of generally curved cross-section about a respective axis extending from a top portion and down across a front portion of the shell.

39. The welding helmet of claim 37, said roll-curved portions including part extending in relatively raised protective relation to the viewing port.

40. The welding helmet of claim 1, further comprising head gear for mounting the helmet on the head of a person.

41. A method of making a welding helmet, comprising
molding composite material in a mold to the shape of the welding helmet shell said molding co mprising forming a plurality of relatively raised and relatively recessed portions in the shell coupled at respective steps to increase stiffness.

42. The method of making a welding helmet of claim 41, said molding comprising curing the composite material during molding.

43. The method of making a welding helmet of claim 41, said molding comprising applying heat to the composite material during molding.

44. The method of making a welding helmet of claim 41, further comprising prior to said molding, pre-shaping the composite material to a shape having a similarity to the mold.

45. The method of making a welding helmet of claim 44, said preshaping comprising draping the composite material over a mandrel.

46. The method of making a welding helmet of claim 41, further comprising supplying the composite material as para-aramid fiber and a thermoset resin.

47. The method of making a welding helmet of claim 46, further comprising maintaining the composite material substantially uncured prior to molding.

48. The method of making a welding helmet of claim 41, further comprising forming a viewing port in the shell.

49. The method of making a welding helmet of claim 48, further comprising mounting a welding lens with respect to the viewing port.

50. The method of making a welding helmet of claim 48, further comprising attaching a trim at said viewing port in sandwich relation to an edge of the shell proximate to the viewing port.

51. The method of making a welding helmet of claim 50, further comprising mounting a welding lens to the trim.

52. The method of making a welding helmet of claim 41, said molding comprising placing composite material in a compression mold having a mold face in the shape of the shell, and urging the composite material against the mold face.

53. The method of making a welding helmet of claim 52, said urging comprising using a flexible bladder to urge the composite material against the mold face.

54. The method of making a welding helmet of claim 52, further comprising applying heat to the composite material during molding.

55. The method of making a welding helmet of claim 52, further comprising assisting in curing the composite material to relatively hard consistency during said molding, said assisting in curing comprising applying heat to the composite material during molding.

56. The method of making a welding helmet of claim 55, said applying heat comprising heating the mold face.

57. The method of making a welding helmet of claim 55, said urging comprising using a flexible bladder to urge the composite material against the mold face, and said applying heat comprising heating the bladder.

58. The method of making a welding helmet of claim 41, said molding comprising molding sheet material consisting of a single sheet of composite material.

59. The method of making a welding helmet of claim 58, said molding comprising molding sheet material consisting of a single sheet of para-aramid fiber material.

60. The method of making a welding helmet of claim 41, said molding comprising molding sheet material consisting of a woven fabric containing a thermoset material.

61. The method of making a welding helmet of claim 41, said forming steps comprising forming a plurality of steps to traverse a curved path along the intersection thereof with respective relatively raised and relatively recessed portions.

62. The method of making a welding helmet of claim 41, further comprising forming roll-curved portions extending generally between the front of the shell and a respective side.

63. The method of making a welding helmet of claim 62, said forming roll-curved portions comprising forming said roll-curved portions of generally curved crosssection about a respective axis extending from a top portion and down across a front portion of the shell.

64. The method of making a welding helmet of claim 63, further comprising forming a viewing port in the shell, and said forming roll-curved portions comprising forming the roll-curved portions with part in relatively raised protective relation to the viewing port.

65. The method of making a welding helmet of claim 63, further comprising mounting a welding lens in the viewing port.

\* \* \* \* \*